US006100064A

United States Patent [19]
Burke et al.

[11] Patent Number: 6,100,064
[45] Date of Patent: Aug. 8, 2000

[54] SECRETED VIRAL PROTEINS USEFUL FOR VACCINES AND DIAGNOSTICS

[75] Inventors: Rae Lyn Burke, San Francisco; Karin Hartog, Piedmont; Carol Pachl, Orinda, all of Calif.

[73] Assignee: Chiron Corporation, Emeryville, Calif.

[21] Appl. No.: 08/282,995

[22] Filed: Jul. 29, 1994

Related U.S. Application Data

[63] Continuation-in-part of application No. 07/671,690, Mar. 26, 1991, which is a continuation-in-part of application No. 07/149,715, Jan. 29, 1988, abandoned, and a continuation-in-part of application No. 08/138,717, Oct. 18, 1993, which is a continuation of application No. 07/993,415, Dec. 21, 1992, abandoned, which is a division of application No. 07/587,179, Sep. 20, 1990, Pat. No. 5,244,792, which is a continuation of application No. 06/921,730, Oct. 20, 1986, abandoned, which is a continuation-in-part of application No. 06/597,784, Apr. 6, 1984, abandoned.

[51] Int. Cl.[7] ............................ C12Q 1/70; C12N 15/85; C12N 1/19; C12N 15/00

[52] U.S. Cl. .................. 435/69.3; 435/172.3; 435/240.1; 435/240.2; 435/282.3; 435/320.1; 536/23.72

[58] Field of Search ............................... 435/69.3, 320.1, 435/172.3, 282.3, 240.1, 240.2; 536/23.72

[56] References Cited

U.S. PATENT DOCUMENTS

| | | | |
|---|---|---|---|
| 5,171,568 | 12/1992 | Burke et al. | 424/89 |
| 5,194,256 | 3/1993 | Rasmussen et al. . | |
| 5,241,053 | 8/1993 | Fujisawa et al. | 424/89 |
| 5,244,792 | 9/1993 | Burke et al. . | |

FOREIGN PATENT DOCUMENTS

| | | |
|---|---|---|
| 0 406 857 A1 | 9/1992 | European Pat. Off. . |
| 0 561 525 A1 | 9/1993 | European Pat. Off. . |
| 2264497 | 2/1993 | United Kingdom . |
| WO 89/07143 | 8/1989 | WIPO . |
| WO 94/25600 | 11/1994 | WIPO . |
| WO 85/04587 | 10/1995 | WIPO . |
| WO 96/17938 | 6/1996 | WIPO . |

OTHER PUBLICATIONS

Stuve et al. 1987 J Virol. 61 (2) pp. 326–335, Feb. 1, 1987.
Kilpatrick et al. 1987 J Biol. Chem. 262 (33) pp. 16116–16121, Nov. 25, 1987.
Despres et al. 1990 Virus Research 16 pp. 59–76, Jan. 1, 1990.
Spaete et al. 1990 J Virol 64 (6) 2922–2931, Jun. 1, 1990.
Fields et al. Ed. Fundamental Virology, Second Edition, Raven Press, NY pp. 929–950, Jan. 1991.
Manservigi et al. J. Virology 64(1): 431–436, 1990.
Wathen et al J. Gen. Virology 70: 2625–2635, 1989.
Rasile et al J. Virology 67(8):4856–4866, 1993.
Pachl et al J. Virology 61(2) 315–325, 1987.
Gething et al Nature 300, 598–603, 1982.
M. Gething et al., "Construction of Influenza Haemagglutinin Genes That Code for for Intracellular and Secreted Forms of the Protein", *Nature* (1982) 300:598–603.

J. Kyte et al., "A Simple Method for Displaying the Hydropathic Character of a Protein", *J. Mol. Biol.* (1982) 157:105–132.
C. Pachl et al., "Expression of Cell–Associated and Secreted Forms of Herpes Simplex Virus Type 1 Glycoprotein gB in Mammalian Cells", *J. Virol.* (1987) 61:315–325.
I. Qadri et al., "Mutations in Conformation–Dependent Domains of Herpes Simplex Virus 1 Glycoprotein B Affect the Antigenic Properties, Dimerization, and Transport of the Molecule", *Virol.* (1991) 180:135–152.
R. Manservigi et al., "Protection from Herpes Simplex Virus Type 1 Lethal and Latent Infections By Secreted Recombinant Glycoprotein B Constitutively Expressed in Human Cells with a BK Virus Episomal Vector", *J. Virol.* (1990) 64:431–436.
M. Stinski et al., "Human Cytomegalovirus: Glycoproteins Associated with Virions and Dense Bodies", *J. Virol.* (1976) 19:594–609.
L. Pereira et al., "Electrophoretic Analysis of Polypeptides Immune Precipitated from Cytomegalovirus–Infected Cell Extracts by Human Sera", *Infect. & Immun.* (1982) 36:933–942.
M. Cranage et al., "Identification of the Human Cytomegalovirus Glycoprotein B Gene and Induction of Neutralizing Antibodies Via Its Expression in Recombinant Vaccinia Virus", *EMBO* (1986) 5:3057–3063.
R. Spaete et al., "Human Cytomegalovirus Strain Towne Glycoprotein B is Processed by Proteolytic Cleavage", *Virol.* (1988) 167:207–405.
L. Rasmussen et al., "Viral Polypeptides Detected By a Complement–Dependent Neutralizing Murine Monoclonal Antibody to Human Cytmegalovirus", *J. Virol.* (1985) 55:274–280.
Partial International Search conducted in corresponding international application No. PCT/US95/09213.
Bos et al., "$NH_2$–terminal Hydrophobic Region of Influenza Virus Neuraminidase Provides the Signal Function in Translocation," *Proc. Natl. Acad. Sci. USA* 81:2327–2331 (1984).

(List continued on next page.)

*Primary Examiner*—Michael P. Woodward
*Assistant Examiner*—Mary K Zeman
*Attorney, Agent, or Firm*—Alisa A. Harbin; Roberta L. Robins; Robert P. Blackburn

[57] ABSTRACT

The present invention relates generally to modified secreted viral proteins, to the genes which express these proteins and to antibodies produced against such proteins, and to the use of these materials in diagnostic and vaccine applications. In particular, the present invention describes deletion of the transmembrane region only and retention of at least part of the cytoplasmic domain itself or fusion with at least part of an alternate cytoplasmic domain. The result will generally be the secretion of proteins which are normally membrane-bound (nonsecretory). This invention greatly increases the efficiency of secretion of the derivative protein. Specific viral proteins of interest include, but are not limited to, those from CMV, HSV, EBV, VZV, HCV, HIV, and influenza.

5 Claims, 21 Drawing Sheets

OTHER PUBLICATIONS

Byars et al., "Vaccinating Guinea Pigs with Recombinant Glycoprotein D of Herpes Simplex Virus in an Efficacious Adjuvant Formulation Elicits Protection Against Vaginal Infection," *Vaccine* 12(3):200–209 (1994).

Navarro et al., "Transport and Secretion of Truncated Derivatives of Herpes Simplex Virus 1 Glycoprotein B," *Virology* 192:234–245 (1993).

Revello et al., "Development and Evaluation of an ELISA Using Secreted Recombinant Glycoprotein B for Determination of IgG Antibody to Herpes Simplex Virus," *Journal of Virological Methods* 34:57–70 (1991).

SECRETED VIRAL PROTEINS USEFUL FOR VACCINES AND DIAGNOSTICS

CROSS-REFERENCES TO RELATED APPLICATIONS

This application is a continuation-in-part of U.S. Ser. No. 07/671,690, filed Mar. 26, 1991 (docket no. 0060.002), pending, which is a continuation-in-part of U.S. Ser. No. 07/149,715, filed Jan. 29, 1988 (docket no. 0060.001), abandoned; and also is a continuation-in-part of U.S. Ser. No. 08/138,717, filed Oct. 18, 1993 (docket no. 0023.005), pending, which is file wrapper continuation of U.S. Ser. No. 07/993,415, filed Dec. 21, 1992 (docket no. 0023.004), abandoned, which is a divisional of 07/587,179, filed Sep. 20, 1990 (docket no. 0023.003), now issued as U.S. Pat. No. 5,244,792, which is a file wrapper continuation of U.S. Ser. No. 06/921,730, filed Oct. 20, 1986 (docket no. 0023.002), abandoned, which is a continuation-in-part of U.S. Ser. No. 06/597,784, filed Apr. 6, 1984 (docket no. 0023.001), abandoned.

BACKGROUND OF THE INVENTION

1. Field of the Disclosure

The present invention relates generally to modified secreted viral proteins, to the genes which express these proteins and to antibodies produced against such proteins, and to the use of such materials in diagnostic and vaccine applications.

2. Brief Description of Related Art

Recombinantly produced proteins or fragments thereof are currently used in vaccines and immunodiagnostic assays. In order to purify and utilize recombinant protein products from eukaryotic cell expression systems, it is useful to engineer the system such that the molecules of interest are expressed at the highest possible level. Obviously, this is critical for commercial production. Secretion of the protein from cells into the medium is optimal and would eliminate many steps in the purification process, as well as eliminating losses of the material at each step.

Eukaryotic cells have a common mechanism for transporting secretory and some membrane proteins to their final destination utilizing a short predominantly hydrophobic signal peptide, usually near the N-terminal region of the protein in type I glycoproteins. This signal sequence is removed from the protein cotranslationally with the process of transit into the lumen of the endoplasmic reticulum. Membrane-bound proteins also contain a hydrophobic transmembrane anchor sequence within the molecule which, during migration of the protein from the inside to the outside of the cell, traps this region of the protein in the lipid bilayer of the membrane.

Viral glycoproteins can be isolated and purified from the lipid bilayer of cell membranes by solubilizing the membranes in detergent. However, this technique introduces problems with insoluble protein-detergent complexes, and protein-protein complexes which are not trivial to purify. Gething, et al., Nature 300:598–603 (1982) and later researchers have truncated viral proteins on the N-terminal side of the hydrophobic transmembrane anchor sequence (thus including the C-terminal cytoplasmic domain). Such a truncated protein secreted into the medium is already soluble and requires much less purification time and energy than an intracellularly expressed protein.

For the case of membrane glycoproteins, as opposed to cytoplasmic proteins, it is useful to engineer the secretion of a functional derivative into the medium rather than express the protein as a membrane-bound, cell-retained protein. Producing a secreted protein permits the development of continuous production processes in which a cell population is supplied with fresh medium daily in a continuous or episodic fashion and conditioned medium containing the protein of interest is withdrawn daily in a continuous or episodic fashion for recovery of the protein of interest.

Producing a secreted protein also facilitates recovery or purification of the protein for two reasons. First, the solubility of the protein is increased by the removal of the hydrophobic, lipophilic domains. Typically purification of membrane proteins requires the use and continuous presence of detergents, since the protein may only be soluble as a protein-detergent micellular complex, which makes the purification and formulation processes more difficult. Also, solubilization of some membrane glycoproteins requires the use of harsh detergents which denature glycoproteins and may result in their loss of functional activity. Second, cell culture can often be performed in the presence of medium with very low protein contents such that the initial relative concentration or specific activity of the protein of interest is much higher than if the protein is recovered from the cell fraction. Given the higher initial purity of the protein, the fold purification required to obtain a protein of high purity is much lower, fewer purification steps are required, and the resultant overall yield will be higher.

SUMMARY OF THE INVENTION

The present invention is useful for recombinant production of viral proteins in eukaryotic cells, whether insect-, mammalian-, or yeast-derived. This application can be used in cells that express the desired proteins transiently by result of transfection or infection or also in cells that express the protein continuously.

Specifically, the present invention describes deletion of the transmembrane region only and retention of at least part of the cytoplasmic domain itself or fusion with an at least part of alternate cytoplasmic domain. The result will generally be the secretion of proteins which are normally membrane-bound (nonsecretory). This invention greatly increases the efficiency of secretion of the derivative protein.

As such, the invention also includes the polynucleotides encoding such proteins; vectors, host cells, and recombinant expression methods; as well as the modified proteins, antibodies thereto, and vaccines and diagnostics employing such modified proteins.

BRIEF DESCRIPTION OF THE DRAWINGS

FIG. 13 is the construction of plasmid pRL104a.

DETAILED DESCRIPTION OF THE INVENTION

A. General Methodology

Figure 1:
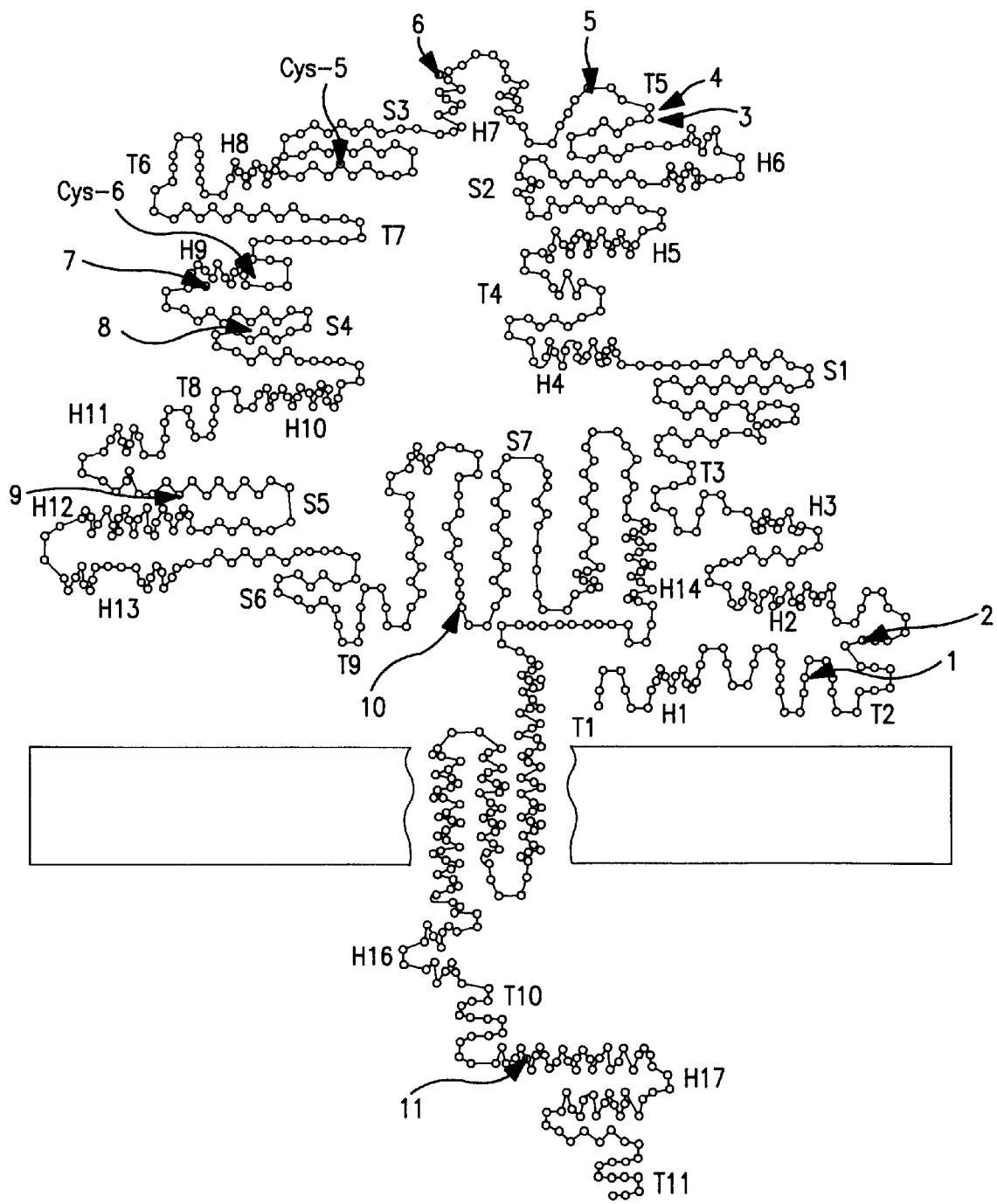
FIG. 1 is the predicted membrane and secondary structure of the HSV-1 gB protein.

The practice of the present invention will employ, unless otherwise indicated, conventional techniques of molecular biology, microbiology, recombinant DNA, immunology, virology, and vaccine development that are within the skill of the art. Such techniques are explained fully in the literature. See e.g., Sambrook, et al., MOLECULAR CLONING; A LABORATORY MANUAL, SECOND EDITION (1989); DNA CLONING, VOLUMES I AND II (D.N Glover ed. 1985); OLIGONUCLEOTIDE SYNTHESIS (M. J. Gait ed, 1984); NUCLEIC ACID HYBRIDIZATON (B. D. Hames & S. J. Higgins eds. 1984); TRANSCRIPTION AND TRANSLATION (B. D. Hames & S. J. Higgins eds. 1984); ANIMAL CELL CULTURE (R. I. Freshney ed. 1986); IMMOBILIZED CELLS AND ENZYMES (IRL Press, 1986); B. Perbal, A PRACTICAL GUIDE TO MOLECULAR CLONING (1984); the series, METHODS IN ENZYMOLOGY (Academic Press, Inc.); GENE TRANSFER VECTORS FOR MAMMALIAN CELLS (J. H. Miller and M. P. Calos eds. 1987, Cold Spring Harbor Laboratory), Methods in Enzymology Vol. 154 and Vol. 155 (Wu and Grossman, and Wu, eds., respectively), Mayer and Walker, eds. (1987), IMMUNOCHEMICAL METHODS IN CELL AND MOLECULAR BIOLOGY (Academic Press, London), Scopes, (1987), PROTEIN PURIFICATION: PRINCIPLES AND PRACTICE, Second Edition (Springer-Verlag, N.Y.), HANDBOOK OF EXPERIMENTAL IMMUNOLOGY, VOLUMES I-IV (D. M. Weir and C. C. Blackwell eds 1986); FUNDAMENTAL VIROLOGY (B. N. Fields and D. M. Knipe, eds., 1991, Raven Press, New York); and VACCINES (R. W. Ellis, ed., 1992, Butterworth-Heinemann, London).

Standard abbreviations for nucleotides and amino acids are used in this specification. All publications, patents, and patent applications cited herein are incorporated by reference.

B. Definitions

By "viral protein" it is meant any protein expressed by a viral genome in which a transmembrane domain is present. By way of example, such viral proteins include, but are not limited to, those from cytomegalovirus (CMV), herpes simplex virus (HSV) types 1 and 2, Epstein-Barr virus (EBV), human herpesviruses (HHV) (e.g., HHV-6), varicella zoster virus (VZV), human immunodeficiency virus (HIV), hepatitis viruses (e.g., Hepatitis C virus (HCV), see EP 318 216, published May 31, 1989; EP 388 232, published Sep. 19, 1990), influenza, measles, mumps, rubella, respiratory syncytial virus (RSV), encephalitis viruses, rabies, pseudorabies, etc.

Typically, such proteins can be divided into four domains beginning at the N-terminus of the protein: (1) a first hydrophobic region, which in membrane glycoproteins may be considered the signal leader sequence direction secretion and/or membrane location; (2) a first variable polarity region, which is often external to the membrane and serves as a recognition sequence (e.g., as a receptor or as an immunogen); (3) a second hydrophobic region, serving as a transmembrane domain ("anchor"); and (4) a second variable polarity region extending to the C-terminus, which is usually cytoplasmic. Thus, the proteins of the present invention are combinations of (1), (2), and (4) above, wherein (1) and/or (4) may be sequences naturally existing with the sequence of (2) or sequences that perform similar functions to those of (1) and (4).

Importantly, the first variable polarity region (2) can serve as an immunogen for the production of antibodies capable of neutralizing the viral pathogen, as a competitive inhibitor for viral infection, as a reagent in immunoassays (either labeled or unlabeled), for the detection of antibodies specific for the viral protein, or the like.

The present invention relates to the deletion of the transmembrane domain and retention of at least part of the cytoplasmic domain or fusion with at least part of a cytoplasmic domain from another viral protein. To determine the exact location of a transmembrane domain in any viral protein, a computer program can be used that formulates a hydropathy scale from the amino acid sequence, utilizing the hydrophobic and hydrophilic properties of each of the 20 amino acids, Kyte, et al., J. Mol. Bio. 157:105–132 (1982). The average hydropathy within a segment of predetermined length of sequence is calculated continuously as the program moves through the sequence. These consecutive hydropathy scores are then plotted from the N-terminus to the C-terminus, and a midpoint line is printed corresponding to a grand hydropathy average of amino acid compositions found in most known sequenced proteins. For proteins of a soluble, globular nature, the interior portions of the protein, as determined by crystallographic studies, correspond to the regions on the hydrophobic side of the midline, while the exterior portions of the protein correspond to the regions on the hydrophilic side of the line. Alternatively, membrane-bound proteins exhibit large uninterrupted regions on the hydrophobic side of the line corresponding to the portion of sequence which is embedded in the lipid bilayer of the membrane. In viral envelope glycoproteins, the transmembrane anchor regions typically contain stretches of 20–27 uncharged, primarily hydrophobic amino acid residues near the C-terminus.

By retention of "at least part" of the cytoplasmic domain is meant the number of amino acids necessary for secretion. Typically, this is at least 5%, more typically at least 10%, and can be 20% or greater. The minimal part will vary depending upon the expression system used and the particular viral protein selected. Often, more than 50% of the cytoplasmic domain will be employed. In some instances, 80–90% of such domain will be maintained or fused.

Further examples of secreted proteins that can be used in the present invention include proteins with minor amino acid variations from the natural amino acid sequence of the protein; in particular, conservative amino acid replacements are contemplated. Conservative replacements are those that take place within a family of amino acids that are related in their side chains. Genetically encoded amino acids are generally divided into four families: (1) acidic=aspartate, glutamate; (2) basic=lysine, arginine, histidine; (3) non-polar=alanine, valine, leucine, isoleucine, proline, phenylalanine, methionine, tryptophan; and (4) uncharged polar=glycine, asparagine, glutamine, cystine, serine, threonine, tyrosine. Phenylalanine, tryptophan, and tyrosine are sometimes classified jointly as aromatic amino acids. For example, it is reasonably predictable that an isolated replacement of a leucine with an isoleucine or valine, an aspartate with a glutamate, a threonine with a serine, or a similar conservative replacement of an amino acid with a structurally related amino acid will not have a major effect on the biological activity. Proteins having substantially the same amino acid sequence as the protein but possessing minor amino acid substitutions that do not substantially affect the functional aspects are within the definition of the protein.

A significant advantage of producing the protein by recombinant DNA techniques rather than by isolating and purifying a protein from natural sources is that equivalent quantities of the protein can be produced by using less starting material than would be required for isolating the protein from a natural source. Producing the protein by recombinant techniques also permits the protein to be isolated in the absence of some molecules normally present in cells. Indeed, protein compositions entirely free of any trace of human protein contaminants can readily be produced because the only human protein produced by the recombinant non-human host is the recombinant protein at issue. Potential viral agents from natural sources and viral components pathogenic to humans are also avoided. Additionally, employing the present invention allows for high levels of protein secretion.

The term "recombinant polynucleotide" as used herein intends a polynucleotide of genomic, cDNA, semisynthetic, or synthetic origin which, by virtue of its origin or manipulation: (1) is not associated with all or a portion of a polynucleotide with which it is associated in nature, (2) is linked to a polynucleotide other than that to which it is linked in nature, or (3) does not occur in nature. Thus, this term also encompasses the situation wherein the viral genes are genetically modified (e.g., through mutagenesis) to produce one or more altered proteins.

The term "polynucleotide" as used herein refers to a polymeric form of a nucleotide of any length, preferably deoxyribonucleotides, and is used inter-changeably herein with the terms "oligonucleotide" and "oligomer." The term refers only to the primary structure of the molecule. Thus, this term includes double- and single-stranded DNA, as well as antisense polynucleotides. It also includes known types of modifications, for example, the presence of labels which are known in the art, methylation, end "caps," substitution of one or more of the naturally occurring nucleotides with an analog, internucleotide modifications such as, for example, replacement with certain types of uncharged linkages (e.g., methyl phosphonates, phosphotriesters, phosphoamidates, carbamates, etc.) or charged linkages (e.g., phosphorothioates, phosphorodithioates, etc.), introduction of pendant moieties, such as, for example, proteins (including nucleases, toxins, antibodies, signal peptides, poly-L-lysine, etc.), intercalators (e.g., acridine, psoralen, etc.), chelators (e.g., metals, radioactive species, boron, oxidative moieties, etc.), alkylators (e.g., alpha anomeric nucleic acids, etc.).

By "genomic" is meant a collection or library of DNA molecules which are derived from restriction fragments that have been cloned in vectors. This may include all or part of the genetic material of an organism. By "CDNA" is meant a complimentary mRNA sequence that hybridizes to a complimentary strand of MRNA.

As used herein, x is "heterologous" with respect to y if x is not naturally associated with y in the identical manner; i.e., x is not associated with y in nature or x is not associated with y in the same manner as is found in nature.

"Homology" refers to the degree of similarity between x and y. The correspondence between the sequence from one form to another can be determined by techniques known in the art. For example, they can be determined by a direct comparison of the sequence information of the polynucleotide. Alternatively, homology can be determined by hybridization of the polynucleotides under conditions which form stable duplexes between homologous regions (for example, those which would be used prior to $S_1$ digestion), followed by digestion with single-stranded specific nuclease(s), followed by size determination of the digested fragments.

A "vector" is a replicon in which another polynucleotide segment is attached, so as to bring about the replication and/or expression of the attached segment. A "replicon" is any genetic element, e.g., a plasmid, a chromosome, a virus, a cosmid, etc. that behaves as an autonomous unit of polynucleotide replication within a cell; i.e., capable of replication under its own control. This may include selectable markers.

"PCR" refers to the technique of polymerase chain reaction as described in Saiki, et al., Nature 324:163 (1986); and Scharf et al., Science (1986) 233:1076–1078; and U.S. Pat. No. 4,683,195; and U.S. Pat. No. 4,683,202.

"Control sequence" refers to polynucleotide sequences which are necessary to effect the expression of coding sequences to which they are ligated. The nature of such control sequences differs depending upon the host organism; in eukaryotes, generally, such control sequences include promoters and transcription termination sequence. The term "control sequences" is intended to include, at a minimum, all components whose presence is necessary for expression, and may also include additional components whose presence is advantageous, for example, leader sequences and fusion partner sequences.

"Operably linked" refers to a juxtaposition wherein the components so described are in a relationship permitting them to function in their intended manner. A control sequence "operably linked" to a coding sequence is ligated in such a way that expression of the coding sequence is achieved under conditions compatible with the control sequences.

An "open reading frame" (ORF) is a region of a polynucleotide sequence which encodes a protein; this region may represent a portion of a coding sequence or a total coding sequence.

A "coding sequence" is a polynucleotide sequence which is translated into a protein, usually via mRNA, when placed under the control of appropriate regulatory sequences. The boundaries of the coding sequence are determined by a translation start codon at the 5'-terminus and a translation stop codon at the 3'-terminus. A coding sequence can include, but is not limited to, CDNA, and recombinant polynucleotide sequences.

As used herein, the term "protein" or "polypeptide" refers to a polymer of amino acids and does not refer to a specific length of the product; thus, peptides, oligopeptides, polypeptides, proteins, and polyproteins, as well as fragments of these, are included within this definition. This term also does not refer to or exclude post expression modifications of the protein, for example, glycosylations, acetylations, phosphorylations and the like. Included within the definition are, for example, proteins containing one or more analogs of an amino acid (including, for example, unnatural amino acids, etc.), proteins with substituted linkages, as well as other modifications known in the art, both naturally occurring and non-naturally occurring.

A polypeptide or protein or amino acid sequence "derived from" a designated nucleic acid sequence refers to a polypeptide having an amino acid sequence identical to that of a polypeptide encoded in the sequence, or a portion thereof wherein the portion consists of at least 3–5 amino acids, and more preferably at least 8–10 amino acids, and even more preferably at least 11–15 amino acids, or which is immunologically identifiable with a polypeptide encoded in the sequence. This terminology also includes a polypeptide expressed from a designated nucleic acid sequence.

"Immunogenic" refers to the ability of a polypeptide to cause a humoral and/or cellular immune response, whether alone or when linked to a carrier, in the presence or absence of an adjuvant. "Neutralization" refers to an immune response that blocks the infectivity, either partially or fully, of an infectious agent.

"Epitope" refers to an antigenic determinant of a peptide, polypeptide, or protein; an epitope can comprise 3 or more amino acids in a spatial conformation unique to the epitope. Generally, an epitope consists of at least 5 such amino acids and, more usually, consists of at least 8–10 such amino acids. Methods of determining spatial conformation of amino acids are known in the art and include, for example, x-ray crystallography and 2-dimensional nuclear magnetic resonance. Antibodies that recognize the same epitope can be identified in a simple immunoassay showing the ability of one antibody to block the binding of another antibody to a target antigen.

"Treatment," as used herein, refers to prophylaxis and/or therapy (i.e., the modulation of any disease symptoms). An "individual" indicates an animal that is susceptible to infection by a viral pathogen and includes, but is not limited to, primates, including humans. A "vaccine" is an immunogen, capable of eliciting protection, whether partial or complete, against a viral pathogen.

The viral proteins may be used for producing antibodies, either monoclonal or polyclonal, specific to the proteins. The methods for producing these antibodies are known in the art.

"Recombinant host cells", "host cells," "cells," "cell cultures," and other such terms denote, for example, microorganisms, insect cells, and mammalian cells, that can be, or have been, used as recipients for recombinant vector or other transfer DNA, and include the progeny of the original cell which has been transformed. It is understood that the progeny of a single parental cell may not necessarily be completely identical in morphology or in genomic or total DNA complement as the original parent, due to natural, accidental, or deliberate mutation. Examples for mammalian host cells include Chinese hamster ovary (CHO) and monkey kidney (COS) cells.

Specifically, as used herein, "cell line," refers to a population of cells capable of continuous or prolonged growth and division in vitro. Often, cell lines are clonal populations derived from a single progenitor cell. It is further known in the art that spontaneous or induced changes can occur in karyotype during storage or transfer of such clonal populations. Therefore, cells derived from the cell line referred to may not be precisely identical to the ancestral cells or cultures, and the cell line referred to includes such variants. The term "cell lines" also includes immortalized cells. Preferably, cell lines include nonhybrid cell lines or hybridomas to only two cell types.

As used herein, the term "microorganism" includes prokaryotic and eukaryotic microbial species such as bacteria and fungi, the latter including yeast and filamentous fungi.

"Transformation", as used herein, refers to the insertion of an exogenous polynucleotide into a host cell, irrespective of the method used for the insertion, for example, direct uptake, transduction, f-mating or electroporation. The exogenous polynucleotide may be maintained as a non-integrated vector, for example, a plasmid, or alternatively, may be integrated into the host genome.

By "purified" and "isolated" is meant, when referring to a polypeptide or nucleotide sequence, that the indicated molecule is present in the substantial absence of other biological macromolecules of the same type. The term "purified" as used herein preferably means at least 75% by weight, more preferably at least 85% by weight, more preferably still at least 95% by weight, and most preferably at least 98% by weight, of biological macromolecules of the same type present (but water, buffers, and other small molecules, especially molecules having a molecular weight of less than 1000, can be present).

C. Expression Systems

Once the appropriate coding sequence is isolated, it can be expressed in a variety of different expression systems; for example, preferably mammalian or baculovirus expression systems, as well as yeast systems.

i. Mammalian Expression Systems

Mammalian expression systems are known in the art. A mammalian promoter is any DNA sequence capable of binding mammalian RNA polymerase and initiating the downstream (3') transcription of a coding sequence (e.g. structural gene) into MRNA. A promoter will have a transcription initiating region, which is usually placed proximal to the 5' end of the coding sequence, and a TATA box, usually located 25–30 base pairs (bp) upstream of the transcription initiation site. The TATA box is thought to direct RNA polymerase II to begin RNA synthesis at the correct site. A mammalian promoter will also contain an upstream promoter element, usually located within 100 to 200 bp upstream of the TATA box. An upstream promoter element determines the rate at which transcription is initiated and can act in either orientation, Sambrook et al., Molecular Cloning: A Laboratory Manual (2nd ed. 1989).

Mammalian viral genes are often highly expressed and have a broad host range; therefore sequences encoding mammalian viral genes provide particularly useful promoter sequences. Examples include the SV40 early promoter, mouse mammary tumor virus LTR promoter, adenovirus major late promoter (Ad MLP), and herpes simplex virus promoter. In addition, sequences derived from non-viral genes, such as the murine metallotheionein gene, also provide useful promoter sequences. Expression may be either constitutive or regulated (inducible), depending on the promoter can be induced with glucocorticoid in hormone-responsive cells.

The presence of an enhancer element (enhancer), combined with the promoter elements described above, will usually increase expression levels. An enhancer is a regulatory DNA sequence that can stimulate transcription up to 1000-fold when linked to homologous or heterologous promoters, with synthesis beginning at the normal RNA start site. Enhancers are also active when they are placed upstream or downstream from the transcription initiation site, in either normal or flipped orientation, or at a distance of more than 1000 nucleotides from the promoter, Maniatis et al., Science 236:1237 (1989); Alberts et al. Molecular Biology of the Cell, 2nd ed (1989). Enhancer elements derived from viruses may be particularly useful, because they usually have a broader host range. Examples include the SV40 early gene enhancer, Dijkema et al (1985) EMBO J. 4:761, and the enhancer/promoters derived from the long terminal repeat (LTR) of the Rous Sarcoma Virus, Gorman et al. (1982) Proc. Natl. Acad. Sci. 79:6777, and from human cytomegalovirus, Boshart et al. (1985) Cell 41:5221. Additionally, some enhancers are regulatable and become active only in the presence of an inducer, such as a hormone or metal ion, Sassone-Corsi et al. (1986) Trends Genet. 2:215; Maniatis et al. (1987) Science 236:1237.

A DNA molecule may be expressed intracellularly in mammalian cells. A promoter sequence may be directly linked with the DNA molecule, in which case the first amino acid at the N-terminus of the recombinant protein will always be a methionine, which is encoded by the ATG start codon. If desired, the N-terminus may be cleaved from the protein by in vitro incubation with cyanogen bromide.

Alternatively, foreign proteins can also be secreted from the cell into the growth media by creating chimeric DNA molecules that encode a fusion protein comprised of a leader sequence fragment that provides for secretion of the foreign protein in mammalian cells. Preferably, there are processing sites encoded between the leader fragment and the foreign gene that can be cleaved either in vivo or in vitro. The leader sequence fragment usually encodes a signal peptide comprised of hydrophobic amino acids which direct the secretion of the protein from the cell. The adenovirus tripartite leader is an example of a leader sequence that provides for secretion of a foreign protein in mammalian cells.

Usually, transcription termination and polyadenylation sequences recognized by mammalian cells are regulatory regions located 3' to the translation stop codon and thus, together with the promoter elements, flank the coding sequence. The 3' terminus of the mature mRNA is formed by site-specific post-transcriptional cleavage and polyadenylation, Birnstiel et al. (1985) Cell 41:349; Proudfoot and Whitelaw (1988) "Termination and 3' end processing of eukaryotic RNA. In Transcription and splicing (ed. B. D. Hames and D. M. Glover); Proudfoot (1989) Trends Biochem. Sci. 14:105. These sequences direct the transcription of an mRNA which can be translated into the polypeptide encoded by the DNA. Examples of transcription terminator/polyadenylation signals include those derived from SV40, Sambrook et al (1989), Molecular Cloning: A Laboratory Manual.

Some genes may be expressed more efficiently when introns (also called intervening sequences) are present. Several cDNAs, however, have been efficiently expressed from vectors that lack splicing signals (also called splice donor and acceptor sites), see e.g., Gething and Sambrook (1981) Nature 293:620. Introns are intervening noncoding sequences within a coding sequence that contain splice donor and acceptor sites. They are removed by a process called "splicing," following polyadenylation of the primary transcript, Nevins (1983) Annu. Rev. Biochem. 52:441; Green (1986) Annu. Rev. Genet. 20:671; Padgett et al. (1986) Annu. Rev. Biochem. 55:1119; Krainer and Maniatis (1988) "RNA splicing," In Transcription and splicing (ed. B. D. Hames and D. M. Glover).

Usually, the above-described components, comprising a promoter, polyadenylation signal, and transcription termination sequence are put together into expression constructs. Enhancers, introns with functional splice donor and acceptor sites, and leader sequences may also be included in an expression construct, if desired. Expression constructs are often maintained in a replicon, such as an extrachromosomal element (e.g., plasmids) capable of stable maintenance in a host, such as mammalian cells or bacteria. Mammalian replication systems include those derived from animal viruses, which require trans-acting factors to replicate. For example, plasmids containing the replication systems of papovaviruses, such as SV40, Gluzman (1981) Cell 23:175, or polyomavirus, replicate to extremely high copy number in the presence of the appropriate viral T antigen. Additional examples of mammalian replicons include those derived from bovine papillomavirus and Epstein-Barr virus. Additionally, the replicon may have two replication systems, thus allowing it to be maintained, for example, in mammalian cells for expression and in a procaryotic host for cloning and amplification. Examples of such mammalian-bacteria shuttle vectors include pMT2, Kaufman et al. (1989) Mol. Cell. Biol. 9:946, and pHEBO, Shimizu et al. (1986) Mol. Cell. Biol. 6:1074.

The transformation procedure used depends upon the host to be transforned. Methods for introduction of heterologous polynucleotides into mammalian cells are known in the art and include dextran-mediated transfection, calcium phosphate precipitation, polybrene mediated transfection, protoplast fusion, electroporation, encapsulation of the polynucleotide(s) in liposomes, and direct microinjection of the DNA into nuclei.

Mammalian cell lines available as hosts for expression are known in the art and include many immortalized cell lines available from the American Type Culture Collection (ATCC), including but not limited to, Chinese hamster ovary (CHO) cells, HeLa cells, baby hamster kidney (BHK) cells, monkey kidney cells (COS), human hepatocellular carcinoma cells (e.g., Hep G2), and a number of other cell lines.

ii. Baculovirus Expression Systems

The polynucleotide encoding the protein can also be inserted into a suitable insect expression vector, and is operably linked to the control elements within that vector. Vector construction employs techniques which are known in the art.

Generally, the components of the expression system include a transfer vector, usually a bacterial plasmid, which contains both a fragment of the baculovirtis genome, and a convenient restriction site for insertion of the heterologous gene or genes to be expressed; a wild type baculovirus with a sequence homologous to the baculovirus-specific fragment in the transfer vector (this allows for the homologous recombination of the heterologous gene in to the baculovirus genome); and appropriate insect host cells and growth media.

After inserting the DNA sequence encoding the protein into the transfer vector, the vector and the wild type viral genome are transfected into an insect host cell where the vector and viral genome are allowed to recombine. The packaged recombinant virus is expressed and recombinant plaques are identified and purified. Materials and methods for baculovirus/insect cell expression systems are commercially available in kit form from, inter alia, Invitrogen, San Diego Calif. ("MaxBac" kit). These techniques are generally known to those skilled in the art and fully described in Summers and Smith, Texas Agricultural Experiment Station Bulletin No. 1555 (1987) (hereinafter "Summers and Smith").

Prior to inserting the DNA sequence encoding the protein into the baculovirus genome, the above-described components, comprising a promoter, leader (if desired), coding sequence of interest, and transcription termination sequence, are usually assembled into an intermediate transplacement construct (transfer vector). This construct may contain a single gene and operably linked regulatory elements; multiple genes, each with its owned set of operably linked regulatory elements; or multiple genes, regulated by the same set of regulatory elements. Intermediate transplacement constructs are often maintained in a replicon, such as an extrachromosomal element (e.g., plasmids) capable of stable maintenance in a host, such as a bacterium. The replicon will have a replication system, thus allowing it to be maintained in a suitable host for cloning and amplification.

Currently, the most commonly used transfer vector for introducing foreign genes into AcNPV is pAc373. Many other vectors, known to those of skill in the art, have also been designed. These include, for example, pVL985 (which alters the polyhedrin start codon from ATG to ATT, and which introduces a BamHI cloning site 32 basepairs downstream from the ATT; see Luckow and Summers, Virology (1989) 17:31.

The plasmid usually also contains the polyhedron polyadenylation signal (Miller et al. (1988) Ann. Rev. Microbiol., 42:177) and a procaryotic ampicillin-resistance (amp) gene and origin of replication for selection and propagation in E. coli.

Baculovirus transfer vectors usually contain a baculovirus promoter. A baculovirus promoter is any DNA sequence capable of binding a baculovirus RNA polymerase and initiating the downstream (5' to 3') transcription of a coding sequence (e.g. structural gene) into MRNA. A promoter will have a transcription initiation region which is usually placed proximal to the 5' end of the coding sequence. This transcription initiation region usually includes an RNA polymerase binding site and a transcription initiation site. A baculovirus transfer vector may also have a second domain called an enhancer, which, if present, is usually distal to the structural gene. Expression may be either regulated or constitutive.

Structural genes, abundantly transcribed at late times in a viral infection cycle, provide particularly useful promoter sequences. Examples include sequences derived from the gene encoding the viral polyhedron protein, Friesen et al., (1986) "The Regulation of Baculovirus Gene Expression," in: The Molecular Biology of Baculoviruses (ed. Walter Doerfler); EPO Publ. Nos. 127 839 and 155 476; and the gene encoding the p10 protein, Vlak et al., (1988), J. Gen. Virol. 69:765.

DNA encoding suitable signal sequences can be derived from genes for secreted insect or baculovirus proteins, such as the baculovirus polyhedrin gene (Carbonell et al. (1988) Gene, 73:409). Alternatively, since the signals for mammalian cell posttranslational modifications (such as signal peptide cleavage, proteolytic cleavage, and phosphorylation) appear to be recognized by insect cells, and the signals required for secretion and nuclear accumulation also appear to be conserved between the invertebrate cells and vertebrate cells, leaders of non-insect origin, such as those derived from genes encoding human α-interferon, Maeda et al., (1985), Nature 315:592; human gastrin-releasing peptide, Lebacq-Verheyden et al., (1988), Molec. Cell. Biol. 8:3129; human IL-2, Smith et al., (1985) Proc. Nat'l Acad. Sci. USA, 82:8404; mouse IL-3, (Miyajima et al., (1987) Gene 58:273; and human glucocerebrosidase, Martin et al. (1988) DNA 7:99, can also be used to provide for secretion in insects.

A recombinant polypeptide or polyprotein may be expressed intracellularly or, if it is expressed with the proper regulatory sequences, it can be secreted. Good intracellular expression of nonfused foreign proteins usually requires heterologous genes that ideally have a short leader sequence containing suitable translation initiation signals preceding an ATG start signal. If desired, methionine at the N-terminus may be cleaved from the mature protein by in vitro incubation with cyanogen bromide.

Alternatively, recombinant polyproteins or proteins which are not naturally secreted can be secreted from the insect cell by creating chimeric DNA molecules that encode a fusion protein comprised of a leader sequence fragment that provides for secretion of the foreign protein in insects. The leader sequence fragment usually encodes a signal peptide comprised of hydrophobic amino acids which direct the translocation of the protein into the endoplasmic reticulum.

After insertion of the DNA sequence and/or the gene encoding the expression product precursor of the protein, an insect cell host is co-transformed with the heterologous DNA of the transfer vector and the genomic DNA of wild type baculovirus—usually by co-transfection. The promoter and transcription termination sequence of the construct will usually comprise a 2–5 kbp section of the baculovirus genome. Methods for introducing heterologous DNA into the desired site in the baculovirus virus are known in the art. (See Summers and Smith; Ju et al. (1987); Smith et al., Mol. Cell. Biol. (1983) 3:2156; and Luckow and Summers (1989)). For example, the insertion can be into a gene such as the polyhedrin gene, by homologous double crossover recombination; insertion can also be into a restriction enzyme site engineered into the desired baculovirus gene. Miller et al., (1989), Bioessays 4:91.

The DNA sequence, when cloned in place of the polyhedrin gene in the expression vector, is flanked both 5' and 3' by polyhedrin-specific sequences and is positioned downstream of the polyhedrin promoter.

The newly formed baculovirus expression vector is subsequently packaged into an infectious recombinant baculovirus. Homologous recombination occurs at low frequency (between about 1% and about 5%); thus, the majority of the virus produced after cotransfection is still wild-type virus. Therefore, a method is necessary to identify recombinant viruses. An advantage of the expression system is a visual screen allowing recombinant viruses to be distinguished. The polyhedrin protein, which is produced by the native virus, is produced at very high levels in the nuclei of infected cells at late times after viral infection. Accumulated polyhedrin protein forms occlusion bodies that also contain embedded particles. These occlusion bodies, up to 15 $\mu$m in size, are highly refractile, giving them a bright shiny appearance that is readily visualized under the light microscope. Cells infected with recombinant viruses lack occlusion bodies. To distinguish recombinant virus from wild-type virus, the transfection supernatant is plagued onto a monolayer of insect cells by techniques known to those skilled in the art. Namely, the plaques are screened under the light microscope for the presence (indicative of wild-type virus) or absence (indicative of recombinant virus) of occlusion bodies. "Current Protocols in Microbiology" Vol. 2 (Ausubel et al. eds) at 16.8 (Supp. 10, 1990); Summers and Smith; Miller et al. (1989).

Recombinant baculovirus expression vectors have been developed for infection into several insect cells. For example, recombinant baculoviruses have been developed for, inter alia: Aedes aegypti, Autographa californica, Bombyx mori, Drosophila melanogaster, Spodoptera frugiperda, and Trichoplusia ni (PCT Pub. No. WO 89/046699; Carbonell et al., (1985) J. Virol. 56:153; Wright (1986) Nature 321:718; Smith et al., (1983) Mol. Cell. Biol. 3:2156; and see generally, Fraser, et al. (1989) In Vitro Cell. Dev. Biol. 25:225).

Cells and cell culture media are commercially available for both direct and fusion expression of heterologous polypeptides in a baculovirus/expression system; cell culture technology is generally known to those skilled in the art. See, e.g., Summers and Smith.

The modified insect cells may then be grown in an appropriate nutrient medium, which allows for stable maintenance of the plasmid(s) present in the modified insect host. Where the expression product gene is under inducible control, the host may be grown to high density, and expression induced. Alternatively, where expression is constitutive, the product will be continuously expressed into the medium and the nutrient medium must be continuously circulated, while removing the product of interest and augmenting depleted nutrients. The product may be purified by such techniques as chromatography, e.g., HPLC, affinity chromatography, ion exchange chromatography, etc.; electrophoresis; density gradient centrifugation; solvent extraction, or the like. As appropriate, the product may be further purified, as required, so as to remove substantially any insect proteins which are also secreted in the medium or result from lysis of insect cells, so as to provide a product which is at least substantially free of host debris, e.g., proteins, lipids and polysaccharides.

In order to obtain protein expression, recombinant host cells derived from the transformants are incubated under conditions which allow expression of the recombinant protein encoding sequence. These conditions will vary, dependent upon the host cell selected. However, the conditions are readily ascertainable to those of ordinary skill in the art, based upon what is known in the art.

iii. Yeast Expression Systems

Yeast expression systems are also known to one of ordinary skill in the art. Although less preferred in the present invention, such systems may be used. For a general review of yeast expression, see Barr et al. (eds.), Yeast Genetic Engineering, Butterworths, London (1989).

D. Vaccines

Each of the viral proteins discussed herein may be used as a sole vaccine candidate or in combination with one or more other antigens, the latter either from the same viral pathogen or from another pathogenic source or sources. These vaccines may either be prophylactic (to prevent infection) or therapeutic (to treat disease after infection).

Such vaccines comprise viral antigen or antigens, usually in combination with "pharmaceutically acceptable carriers", which include any carrier that does not itself induce the production of antibodies harmful to the individual receiving the composition. Suitable carriers are typically large, slowly metabolized macromolecules such as proteins, polysaccharides, polylactic acids, polyglycolic acids, polymeric amino acids, amino acid copolymers, lipid aggregates (such as oil droplets or liposomes), and inactive virus particles. Such carriers are well known to those of ordinary skill in the art. Additionally, these carriers may function as immunostimulating agents ("adjuvants"). Furthermore, the antigen may be conjugated to a bacterial toxoid, such as a toxoid from diphtheria, tetanus, cholera, H. pylori, etc. pathogens.

Preferred adjuvants to enhance effectiveness of the composition include, but are not limited to: (1) aluminum salts (alum), such as aluminum hydroxide, aluminum phosphate, aluminum sulfate, etc; (2) oil-in-water emulsion formulations (with or without other specific immunostimulating agents such as muramyl peptides (see below) or bacterial cell wall components), such as for example (a) MF59 (PCT Publ. No. WO 90/14837), containing 5% Squalene, 0.5% Tween 80, and 0.5% Span 85 (optionally containing various amounts of MTP-PE (see below), although not required) formulated into submicron particles using a microfluidizer such as Model 110Y microfluidizer (Microfluidics, Newton, Mass.), (b) SAF, containing 10% Squalane, 0.4% Tween 80, 5% pluronic-blocked polymer L121, and thr-MDP (see below) either microfluidized into a submicron emulsion or vortexed to generate a larger particle size emulsion, and (c) Ribi™ adjuvant system (RAS), (Ribi Immunochem, Hamilton, Mont.) containing 2% Squalene, 0.2% Tween 80, and one or more bacterial cell wall components from the group consisting of monophosphorylipid A (MPL), trehalose dimycolate (TDM), and cell wall skeleton (CWS), preferably MPL+CWS (Detox™); (3) saponin adjuvants, such as Stimulon™ (Cambridge Bioscience, Worcester, Mass.) may be used or particles generated therefrom such as ISCOMs (immunostimulating complexes); (4) Complete Freunds Adjuvant (CFA) and Incomplete Freunds Adjuvant (IFA); (5) cytokines, such as interleukins (IL-1, IL-2, etc.), macrophage colony stimulating factor (M-CSF), tumor necrosis factor (TNF), etc; and (6) other substances that act as immunostimulating agents to enhance the effectiveness of the composition. Alum and MF59 are preferred.

As mentioned above, muramyl peptides include, but are not limited to, N-acetyl-muramyl-L-threonyl-D-isoglutamine (thr-MDP), N-acetyl-normuramyl-L-alanyl-D-isoglutamine (nor-MDP), N-acety lmuramyl-L-alanyl-D-isoglutaminyl-L-alanine-2-(1'-2'-dipalmitoyl-sn-glycero-3-hydroxyphosphoryloxy)-ethylamine (MTP-PE), etc.

The immunogenic compositions (e.g., the antigen, phannaceutically acceptable carrier, and adjuvant) typically will contain diluents, such as water, saline, glycerol, ethanol, etc. Additionally, auxiliary substances, such as wetting or emulsifying agents, Ph buffering substances, and the like, may be present in such vehicles.

Typically, the immunogenic compositions are prepared as injectables, either as liquid solutions or suspensions; solid forms suitable for solution in, or suspension in, liquid vehicles prior to injection may also be prepared. The preparation also may be emulsified or encapsulated in liposomes for enhanced adjuvant effect, as discussed above under pharmaceutically acceptable carriers.

Immunogenic compositions used as vaccines comprise an immunologically effective amount of the antigenic polypeptides, as well as any other of the above-mentioned components, as needed. By "immunologically effective amount," it is meant that the administration of that amount to an individual, either in a single dose or as part of a series, is effective for treatment or prevention. This amount varies depending upon the health and physical condition of the individual to be treated, the taxonomic group of individual to be treated (e.g., nonhuman primate, primate, etc.), the capacity of the individual's immune system to synthesize antibodies, the degree of protection desired, the formulation of the vaccine, the treating doctor's assessment of the medical situation, and other relevant factors. It is expected that the amount will fall in a relatively broad range that can be determined through routine trials.

The immunogenic compositions are conventionally administered parenterally, e.g., by injection, either subcutaneously or intramuscularly. Additional formulations suitable for other modes of administration include oral and pulmonary formulations, suppositories, and transdermal applications. Oral formulations may be preferred for certain viral proteins. Dosage treatment may be a single dose schedule or a multiple dose schedule. The vaccine may be administered in conjunction with other immunoregulatory agents.

E. Immunodiagnostic Assays

Viral antigens of the present invention can be used in immunoassays to detect antibody levels (or conversely antibodies can be used to detect antigen levels). Immunoassays based on well defined, recombinant antigens can be developed to replace the invasive diagnostics methods that are used today. Antibodies to proteins within biological samples, including for example, blood or serum samples, can be detected. Design of the immunoassays is subject to a great deal of variation, and a variety of these are known in the art. Protocols for the immunoassay may be based, for example, upon competition, or direct reaction, or sandwich type assays. Protocols may also, for example, use solid supports, or may be by immunoprecipitation. Most assays involve the use of labeled antibody or polypeptide; the labels may be, for example, fluorescent, chemiluminescent, radioactive, or dye molecules. Assays which amplify the signals from the probe are also known; examples of which are assays which utilize biotin and avidin, and enzyme-labeled and mediated immunoassays, such as ELISA assays.

Kits suitable for immunodiagnosis and containing the appropriate labeled reagents are constructed by packaging the appropriate materials, including the compositions of the invention, in suitable containers, along with the remaining reagents and materials (for example, suitable buffers, salt solutions, etc.) required for the conduct of the assay, as well as suitable set of assay instructions.

F. Examples

The examples presented below are provided as a further guide to the practitioner of ordinary skill in the art and are not to be construed as limiting the invention in any way.

i. Herpes Simplex Virus (HSV) Proteins a. HSV

Infections caused by HSV constitute an extremely prevalent communicable disease of humans, and the clinical manifestations of infection are diverse ranging from the common occurrence of vesicular, ulcerative lesions on the lip or the genital skin, to the more rare and severe infections including stomatitis, keratoconjunctivitis, meningitis, and encephalitis. These infections are caused by two distinct viruses, HSV-1 and HSV-2. HSV-1 is the predominant cause of oral infections, whereas HSV-2 infections are usually sexually transmitted genital infections. These distinctions are blurred, however, and up to 25% of genital herpes is caused by HSV-1. In general, HSV is a double-stranded DNA virus having a genome of about 150–160 kbp packaged within an icosahedral nucleocapsid enveloped in a membrane. The membrane includes a number of virus-specific glycoproteins, the most abundant of which are gB, gC, gD, and gE, wherein gB and gD are cross-reactive between HSV types 1 and 2. The viral genomes of HSV-1 and HSV-2 are co-linear and have a 50% homology. For some genes, such as the glycoproteins gB and gD, the amino acid identity increases up to 80–90%. The entire HSV-1 genome has been sequenced, McGeoch, D. J., et al., J. Gen. Virol. 69:1531–1574 (1988), and the HSV-2 genome is in progress, Kieff, E. D., et al., J. Virol. 9:738 (1972). Within a virus type, there is a limited (1–2%) strain-to-strain sequence variability of the glycoprotein genes. Strains of HSV include, but are not limited to, 333 and Patton.

The present invention has direct applicability to the production of these, and other HSV glycoproteins, as well as to other HSV proteins having the structure delineated above.

b. HSV gB

The genes encoding gB1 and gB2 were subcloned and sequenced by researchers of the present assignee, see U.S. Pat. No. 5,244,792; Pachl, C., et al., J. Virol. 61:315–325 (1987). A view of the HSV-1 gB protein is given in FIG. 1 to illustrate the secondary structure of the protein and the orientation of the transmembrane region. This figure is taken from Qadri, et al., Virology 135:135–152 (1991) (H, S, and T indicate major helical, sheet, and turn domains, respectively, and sheet domains were numbered from the N-terminus). The gB2 protein is about 904 amino acids in length and contains elements characteristic of a membrane glycoprotein. After cleavage of the predicted 22-amino-acid signal sequence, the mature, non-glycosylated protein has a predicted molecular weight of about 98 kD. (The reader is also referred to Manservigi, et al., J. Virol. 64:431–436 (1990) for later work in this area.)

c. HSV gB2dTM

Figure 2:
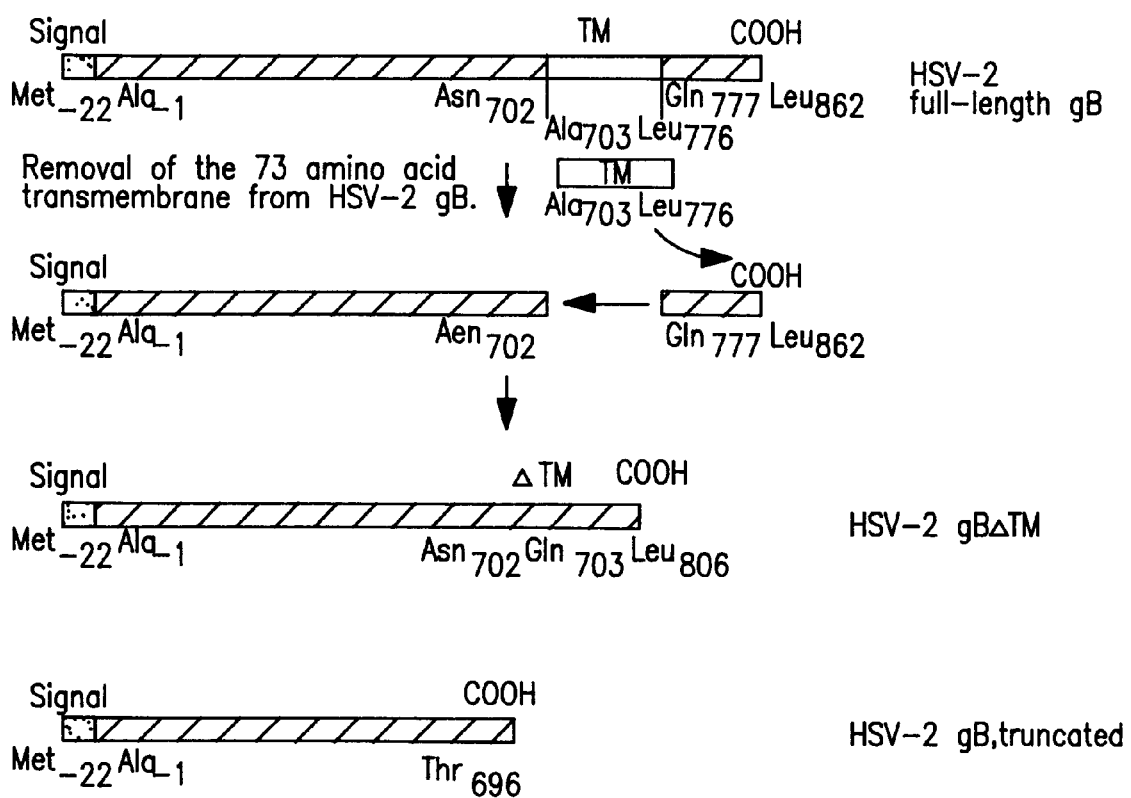
FIG. 2 is a comparison of full-length HSV-2 gB protein and truncated gB protein with the present invention, gB2dTM.
Figure 3:
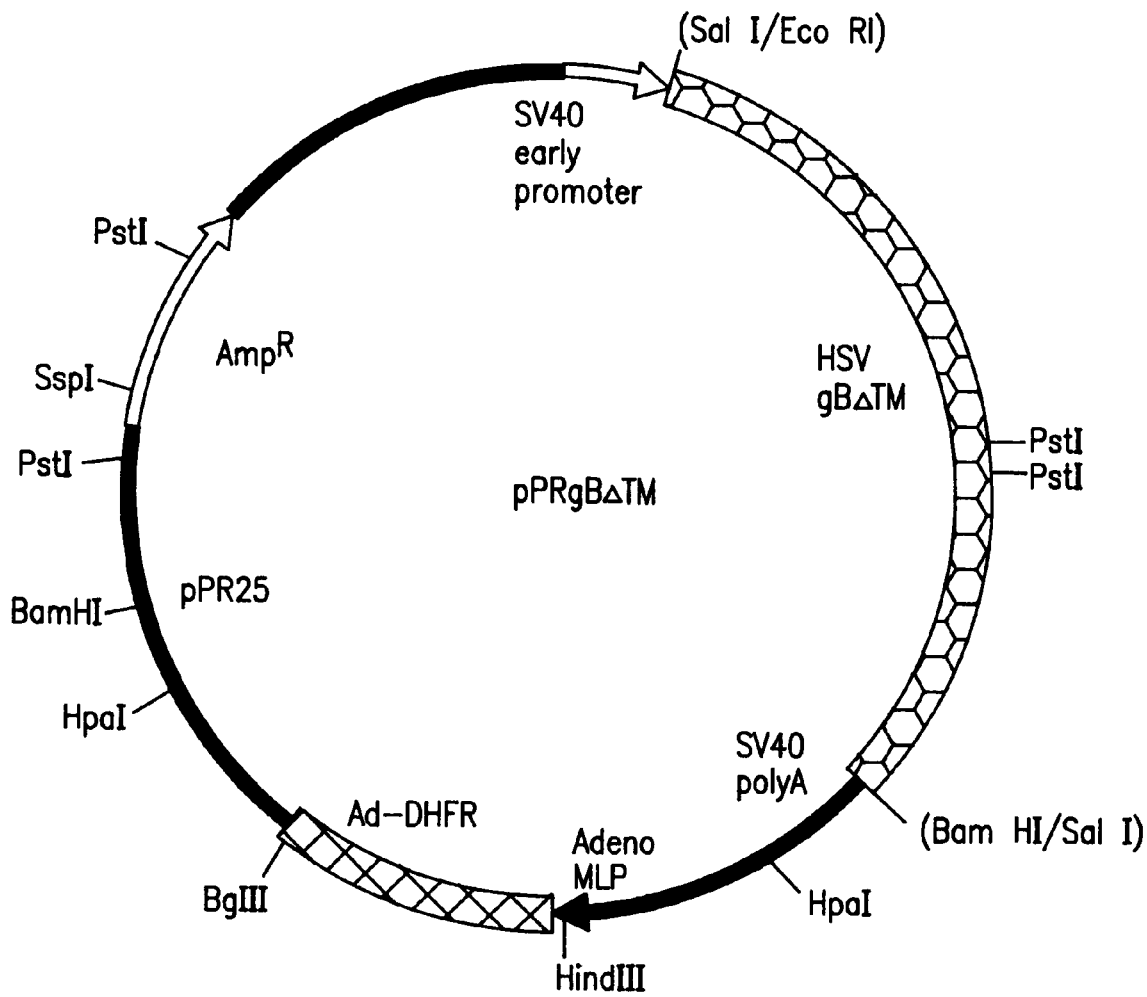
FIG. 3 is the HSV plasmid pPRgBdTM.

Plasmid pPRgBdTM, an expression vector for the HSV-2 gB antigen, contains a modified derivative of the gB gene under the control of the SV40 early promoter (FIG. 3). The gB gene derivative is 808 amino acids in length and lacks the transmembrane (TM) region. FIG. 2 compares full-length HSV-2 gB and truncated gB with the present invention, gB2dTM. FIG. 2 shows both gB2dTM and an intermediate showing the process of removal of the transmembrane domain. This derivative was constructed to improve the secretion efficiency of the gB2 protein compared to truncated gB2 used previously, wherein both the transmembrane domain and the C-terminal region were deleted. Both protein derivatives contain substantially all of the extracellular domain of the gB protein. gB2dTM has two new amino acids, $Gly_{702}$ and $Thr_{703}$, that were inserted as the result of the cloning and the introduction of a KpnI site at the fusion between the extracellular and cytoplasmic domains. Plasmid pPRgBdTM also contains the SV40 origin of replication, the SV40 poly A addition site and the dihydrofolate reductase cDNA under the control of the adenovirus major late promoter (Ad-dhfr). The construction of all plasmids is described in detail below.

d. Construction of plasmid pPRgBdTM

Figure 4:
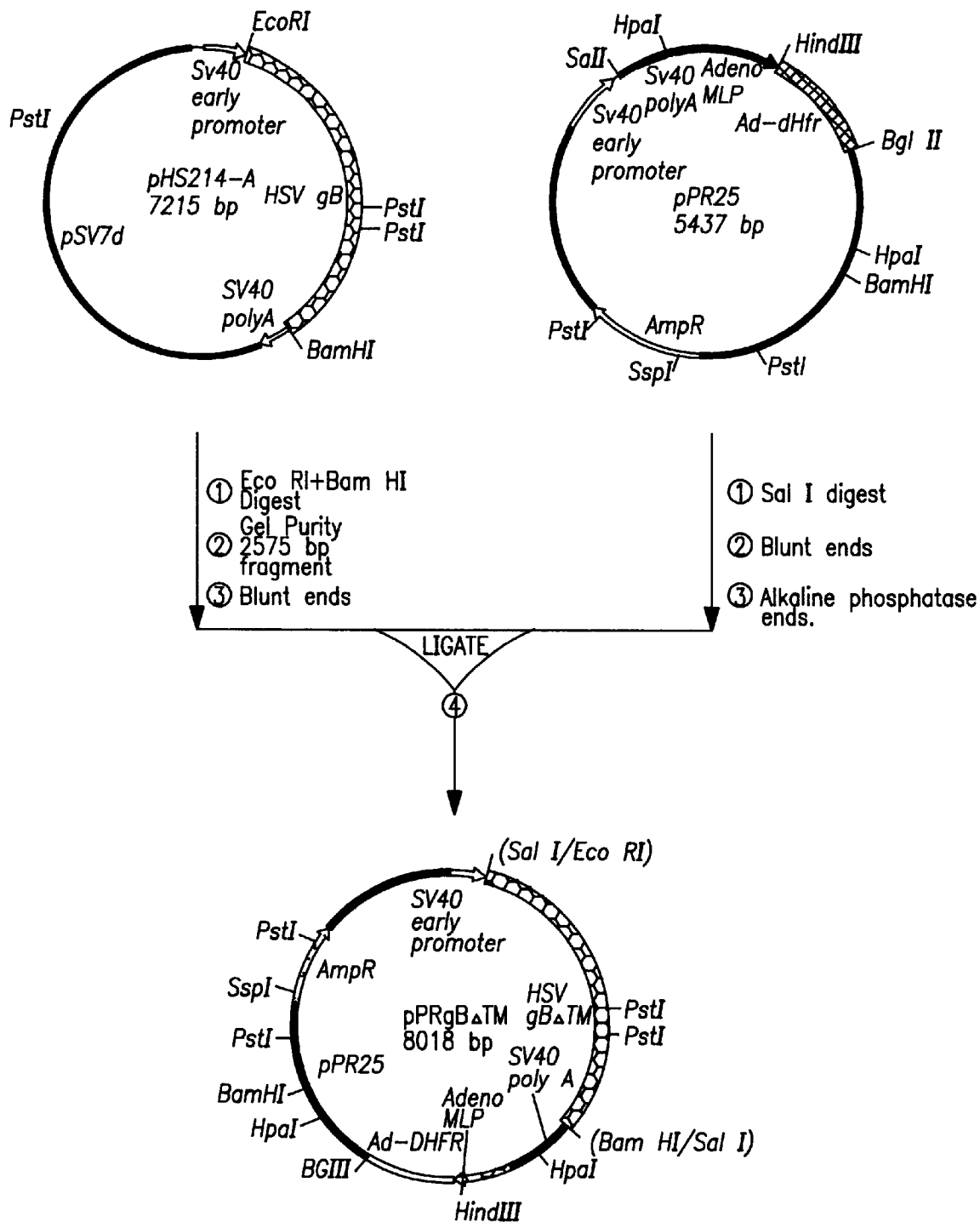
FIG. 4 is the construction of plasmid pPRgBdTM.

The scheme used to construct pPRgBdTM is illustrated in FIG. 4. The gB2dTM derivative gene sequence was obtained as a 2.57 kp EcoRI-BamHI fragment from plasmid pHS214-A. The fragment was incubated with the Klenow fragment of DNA polymerase I to repair the EcoRI and BamHI sites to blunt ends and then was ligated to the mammalian cell expression vector pPR25 that had previously been cut with SalI and the ends repaired to blunt with Klenow DNA polymerase I fragment followed by treatment with alkaline phosphatase. Note that the use of parentheses around a restriction site indicates that the site was lost during the cloning process.

Figure 5:
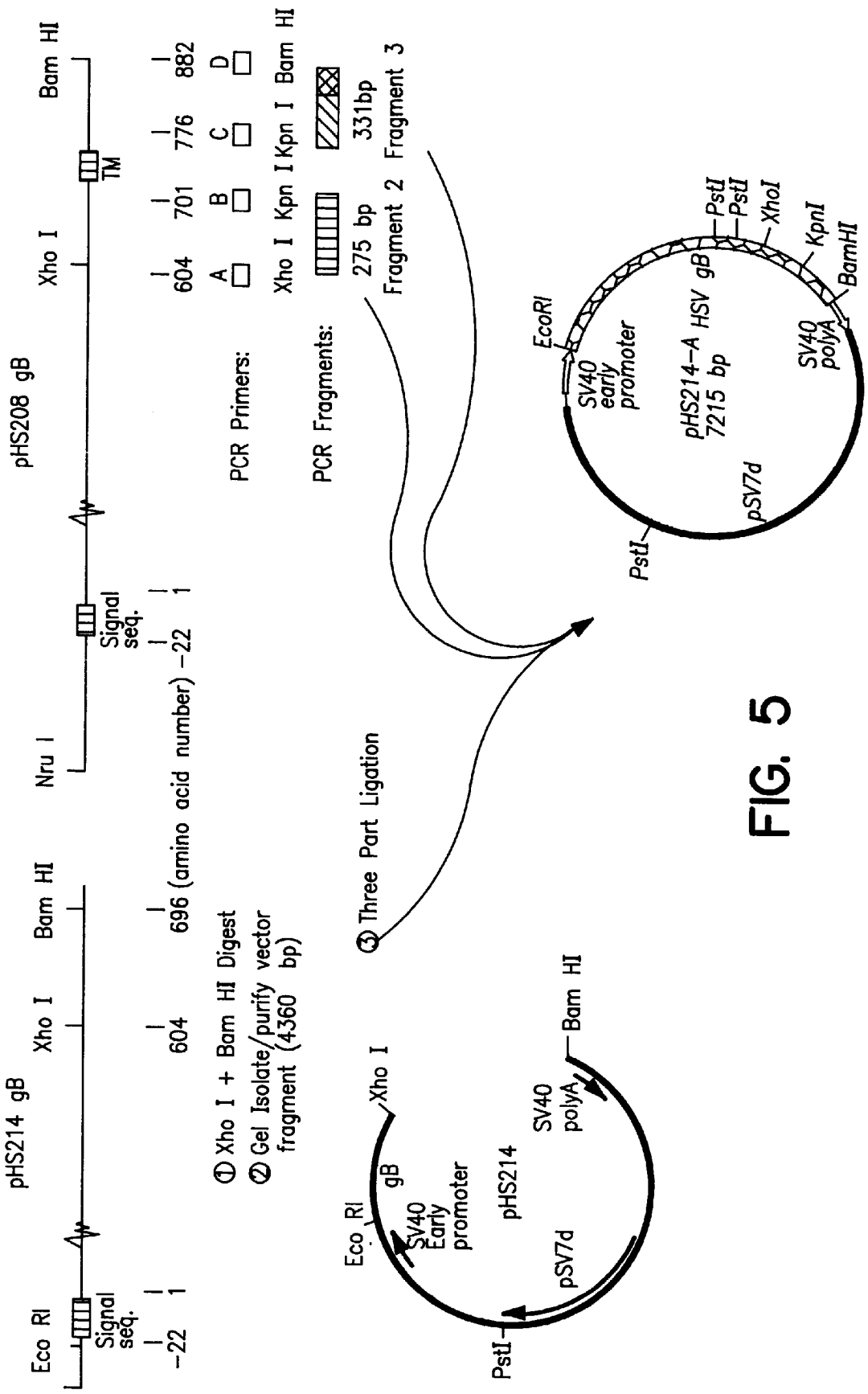
FIG. 5 is the construction of plasmid pHS214-A.

The construction of plasmid pHS214-A is illustrated in FIG. 5. The complete HSV-2 gB sequence is contained within a 3467 bp NruI to BamHI fragment in plasmid pHS208. The gB2 derivative gene, gB2dTM lacking amino acids $Asp_{701}$ to $Gln_{776}$ of the transmembrane domain, was assembled from three fragments: (1) The 5' end of the gB2 gene containing the 22 amino acid signal sequence and 604 amino acids of the extracellular domain, $Ala_1$ through $Ala_{604}$, as well as all of the pSV7d vector sequences including the SV40 promoter, the SV40 polyadenylation site and the sequences required for replication in bacteria was obtained as a 4360 bp XhoI to BamHI fragment from plasmid pHS214; (2) The remainder of the extracellular domain of gB2 from $Leu_{605}$ to $Asp_{701}$ was obtained from plasmid pHS208 as a PCR fragment of 294 bp with primer A containing the natural XhoI site complementary to nucleotide 1870 to 1980 (considering the initial ATG of the gB gene as nucleotide 1) and primer B complementary to nucleotides 2158 to 2169 and containing an introduced KpnI site. This fragment was digested with the restriction enzymes XhoI and KpnI and isolated by agarose gel electrophoresis; and (3) The 3' end of the gB2 gene, comprising the cytoplasmic domain containing amino acids $Gln_{776}$ to the stop codon at amino acid position 883 was prepared from plasmid PHS208 as a 321 bp KpnI to BamHI fragment by using PCR primers C complementary to nucleotides 2395 to 2407 containing the engineered KpnI site and PCR primer D complementary to nucleotides 2698 to 2715 containing the stop codon and the BamHI site. This fragment was digested with the restriction enzymes Kpnl and BamHI and isolated by gel electrophoresis. These three fragments 1, 2 and 3 were ligated together to generate plasmid pHS214-A containing the derivative gB2dTM gene in the expression vector pSV7d.

Figure 6:
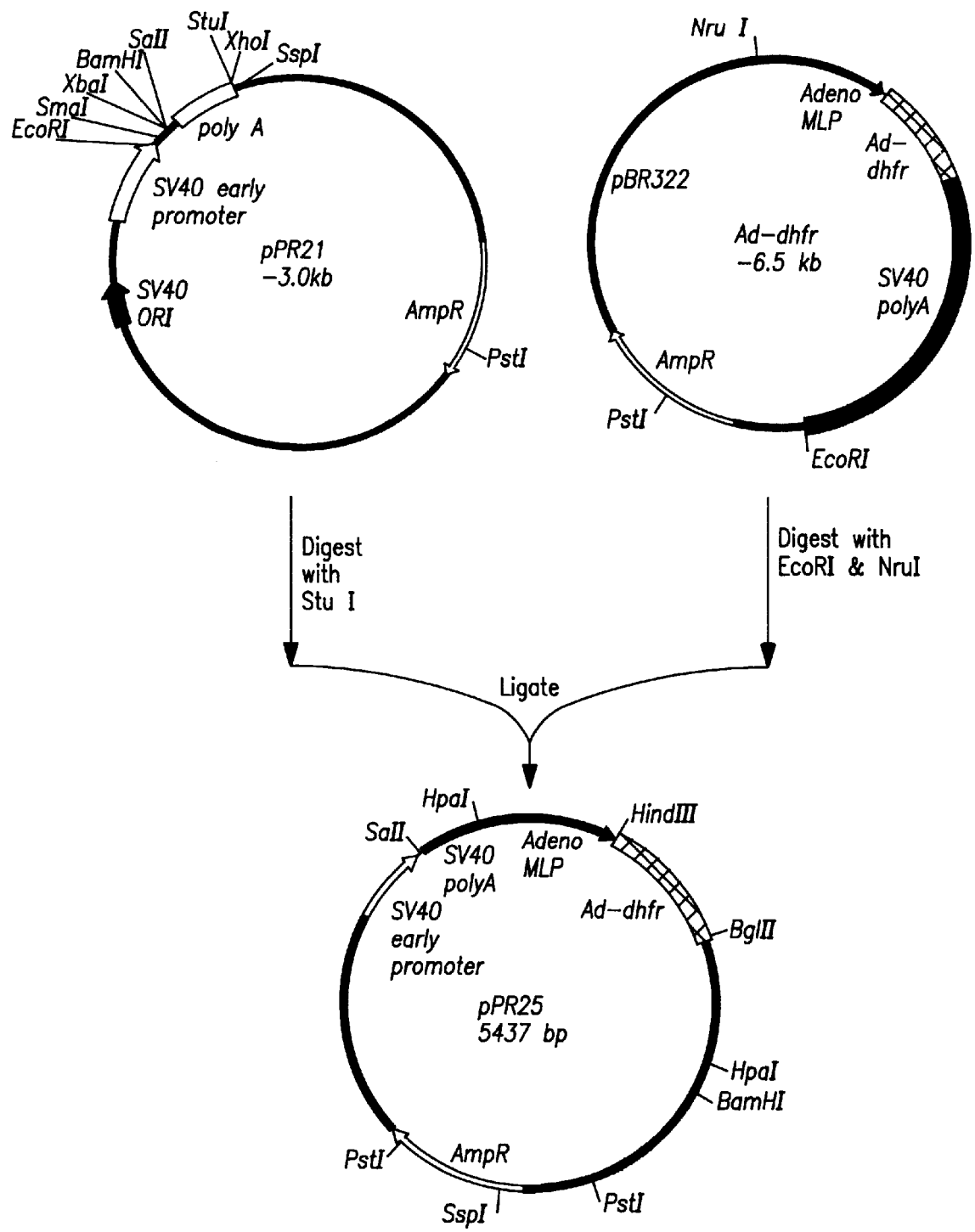
FIG. 6 is the construction of plasmid pPR25.
Figure 7:
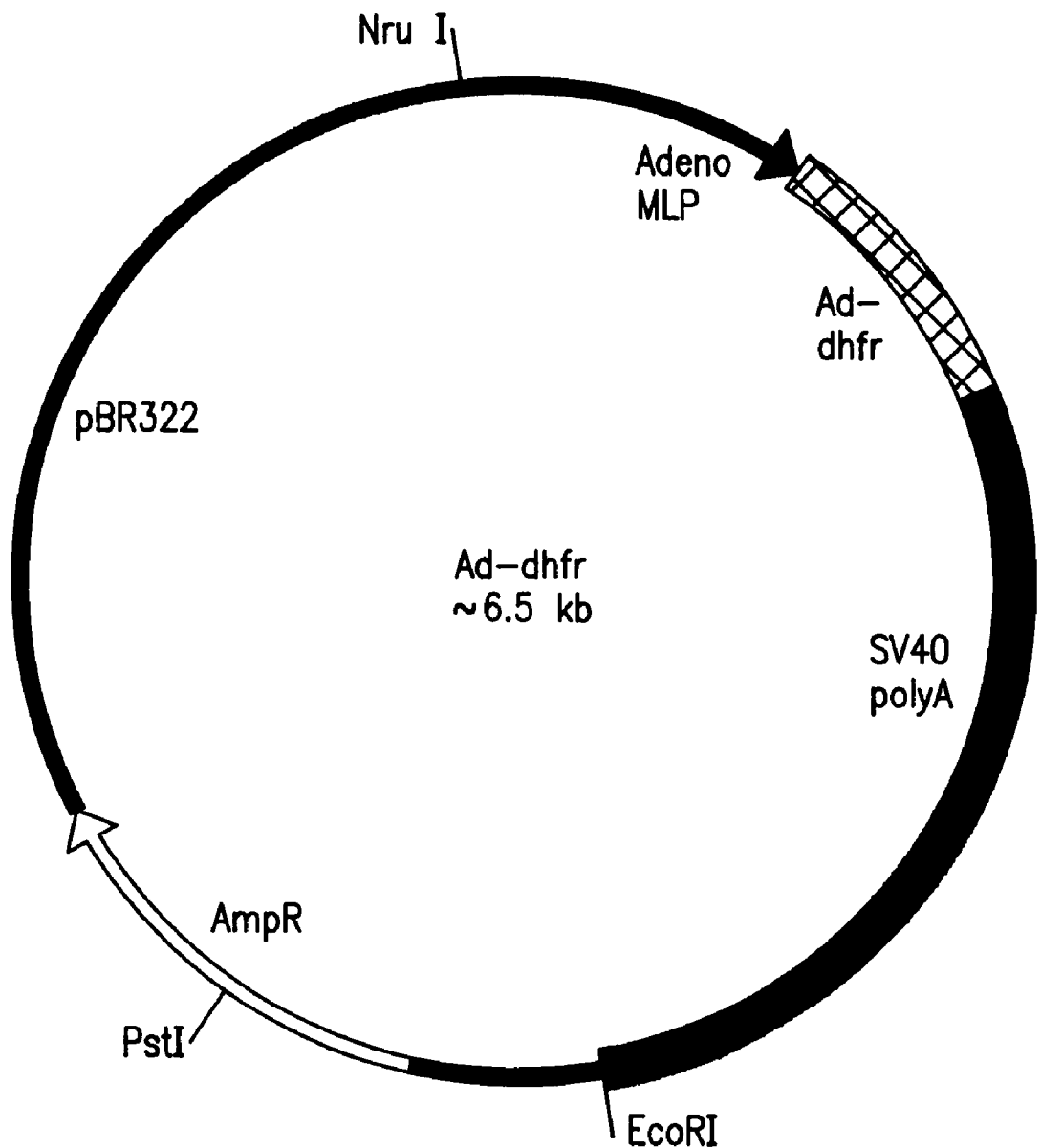
FIG. 7 is the expression vector pAd-dhfr.

Plasmid pPR25 is a mammalian cell expression vector containing the dihydrofolate reductase (dhfr) cDNA under the control of the adenovirus-2 major late promoter (Ad-2 MLP), SV40 DNA encoding the small T antigen intron and polyadenylation sequences. The construction of pPR25, presented in FIG. 6, required the digestion of plasmid pPR21 with StuI and the insertion of a 3388 bp NruI-EcoRI fragment from expression vector, pAd-dhfr (FIG. 7). Plasmid pPR21 was derived from pSV7d (FIGS. 8 and 9) by inserting a synthetic 85-mer, containing the bla promoter and the restriction sites for StuI and XhoI, into the SspI site in the poly linker.

Figure 8:
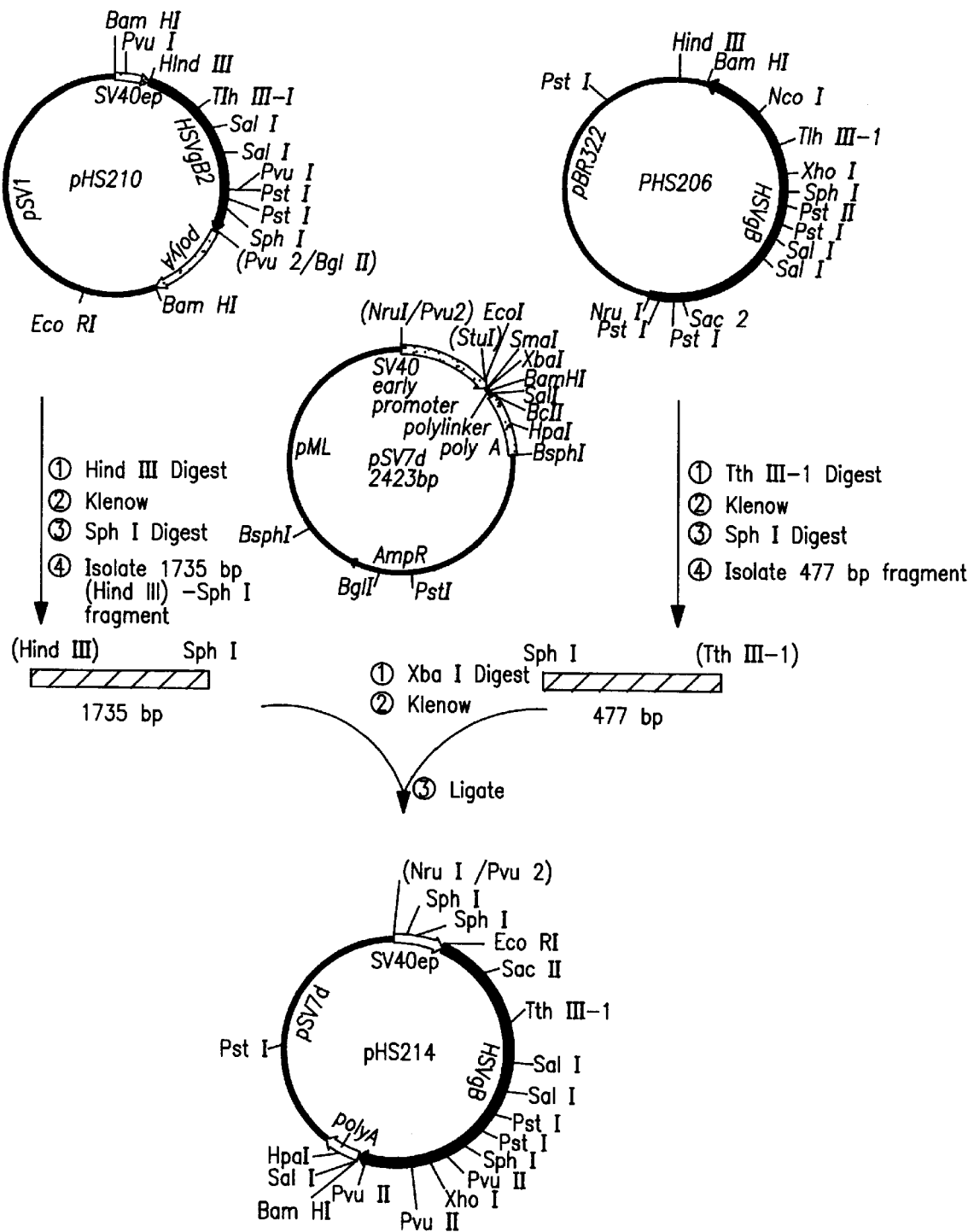
FIG. 8 is the construction of plasmid pHS214.
Figure 9:
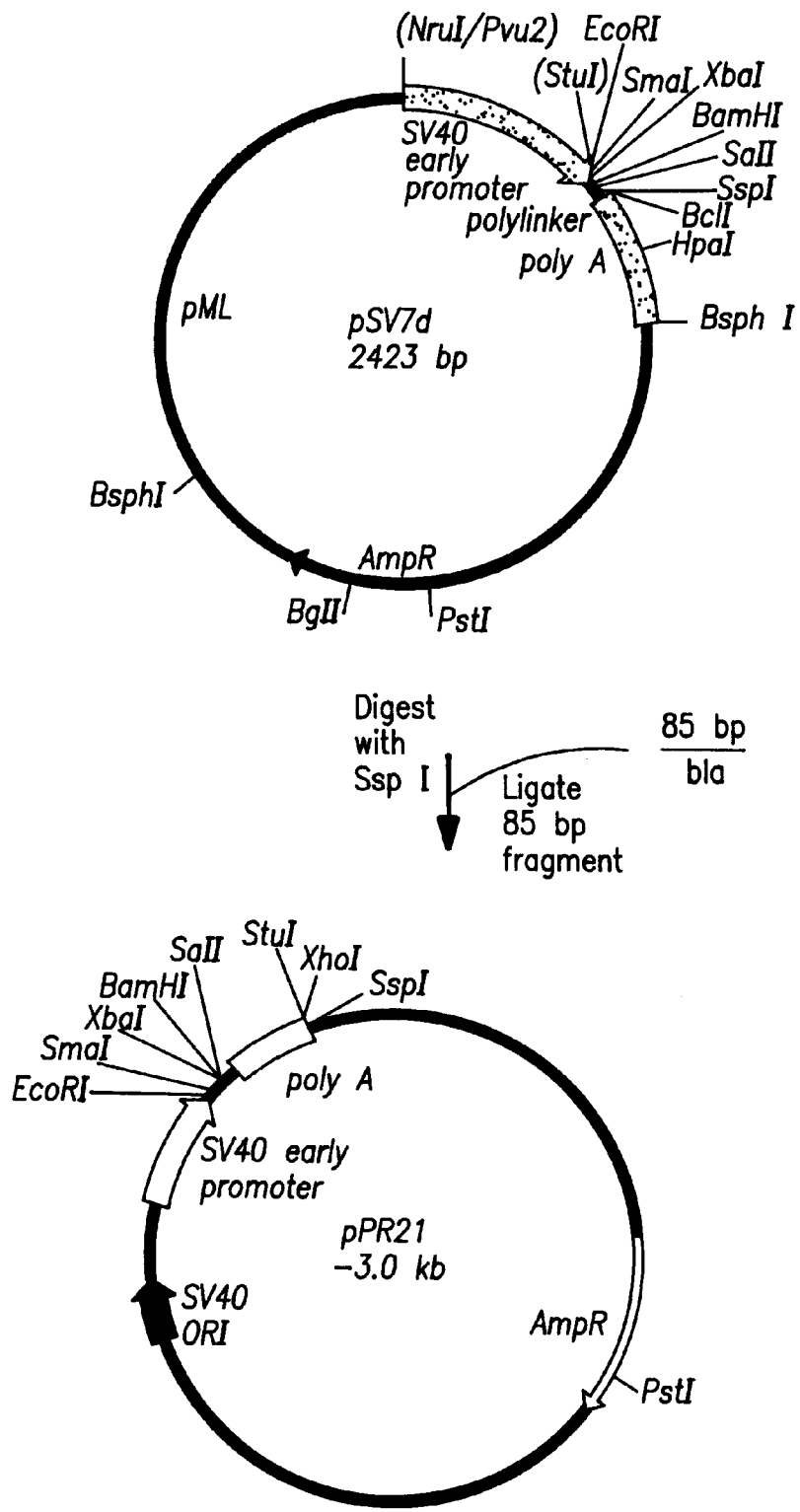
FIG. 9 is the construction of plasmid pPR21.

The scheme used to construct pHS214 is outlined in FIG. 8. The truncated derivative of the gB2 gene was obtained as two fragments which were ligated together into the expression vector. The 3'-end of the coding sequence was obtained from pHS208, a plasmid which contains the entire gB2 gene as a 3.46 kbp NruI-BamHI fragment (8). pHS208 was digested with TthIII and a 1660 bp fragment was isolated. The fragment ends were filled-in with the Klenow fragment of DNA polymerase I, the DNA was digested with SphI and a 477 bp SphI-(TthIII) fragment was isolated containing sequences encoding for gB2 amino acids 560–718.

The 5'-end of the truncated gB2 gene was obtained from pHS210, a plasmid which contains a 1.90 kbp HindIII-PvuII fragment encoding 591 amino acids of the gB2 protein. The gB2 coding region in pHS210 is truncated at a PvuII site, 110 amino acids N-tenrminal to the proposed membrane anchor sequence. pHS210 was digested with HindIII, the fragment ends were filled-in with the Klenow fragment of DNA polymerase I and the DNA was digested with SphI. A 1735 bp (HindIII)-SphI fragment was isolated.

The two gB2 gene fragments isolated above were ligated together the fragment ends were filled with the Klenow fragment of DNA polymerase I and inserted into pSV7d (FIG. 9), previously digested with XbaI and repaired to blunt ends with the Klenow fragment of DNA polymerase I, to generate pHS214.

e. Expression of gB2dTM in mammalian cells pPRgBdTM was transfected into both COS 7 cells and dhfr CHO cells. Expression of the gB2 protein into the culture medium was confirmed by an ELISA as described by Stuve, et al., J. Virol. 61:326–335 (1987). A CHO cell line expressing the secreted gB2dTM was selected for large scale commercial production. For this purpose, CHO cells lacking an endogenous dihydrofolate reductase (gene encoding the dhfr enzyme) were transfected with a DNA plasmid vector containing genes for both dhfr as well as an HSV gB2 derivative, gB2dTM. The transfected cells were grown in selective culture medium such that only cells that expressed dhfr could grow. The level of gB production by these cells was increased by a stepwise process of culture in selective medium containing increasing concentrations of the drug methotrexate (MTX), a noncompetitive inhibitor of dhfr. Cells acquired the ability to grow in the presence of MTX by amplifying the number of copies of the dhfr gene, Alt, F.W., et al., J.Biol.Chem. 235:1357–1370 (1978); Kaufman,R. J., et al., Mol. Cellular Biol. 1:1069–1076 (1981). A second gene, gB2, that was directly linked to the dhfr DNA was also co-amplified, Kaufinan,R. J., et al., J. Mol. Biol. 159:601–621 (1982). This process entailed exposure of cells in a bulk population to selective medium with MTX, selection of 50–400 discrete single colony clones, expansion of the colony cell number by serial passage in 96 well-plates, then 24 well and 6 well plates with concurrent evaluation of gB productivity using an ELISA assay to measure the amount of gB secreted into the culture medium. This process was stopped when no further gains in productivity were observed.

f. Pulse chase secretion efficiency studies for gB2dTM and gB truncated proteins Plasmid pPRgBdTM expressed in a CHO cell line contains the gB2dTM gene encoding a gB derivative protein of 808 amino acids in length and lacking the transmembrane region, as described above. The cell line expressing truncated gB contains plasmid pHS217, identical to pPRgBdTM except that it encodes a 696 amino acid carboxyl terminal truncated gB derivative protein. Both protein derivatives contain substantially all of the extracellular domain of the gB protein.

A study of the efficiency and kinetics of gB2 secretion for the cell line expressing truncated gB as compared with the cell line expressing gB2dTM was performed by incubating the cells for 2 hours in medium containing [$^{35}$S]-methionine and chasing with the addition of an excess of cold methionine for 30 min., 4 hours, or overnight. The gB2 present intracellularly as well as in the medium was immunoprecipitated by a conformational specific monoclonal antibody to gB2 LSPB1. Following a two hour pulse label for the production cell line, all truncated gB2 remained intracellular; there was no protein in the medium. Following a 30 minute chase, there was still no secreted truncated gB2 protein. After a 4 hour chase, approximately 50% of the truncated gB2 appeared in the medium; the remainder of the intracellular material was degraded with 3 bands visible at about 68 kD and at the gel front. After an overnight chase, no additional truncated gB was secreted and all the intracellular truncated gB migrated at the gel front.

The kinetics and efficiency of gB2dTM secretion differed dramatically from this pattern for the gB2dTM cell line. During the 2 hour pulse labeling about 33% of the gB2dTM protein was secreted. During a 30 minute chase, again about ⅓ of the material was secreted. Following a 4 hour chase, about 90% of the protein was secreted and the remaining 10% of intracellular gB2dTM was still intact. After the overnight chase, an additional 5% of the gB2dTM was secreted. Minimal degradation of the remaining 5% of the intracellular gB2dTM was visible at this time point with a band pattern different than truncated gB2 with band sizes of 68 kD, 38 kD and at the gel front for the latter. The most important point was shown by the increase in secreted gB2dTM compared to truncated gB2 after a 4 hour or overnight chase.

The gB2dTM cell line appeared to secrete about 10-fold gB protein more than the cell line expressing gB2. These results suggested that the gB2dTM protein is folded more rapidly and efficiently than the truncated gB2 protein. As a result, it is secreted more rapidly and a greater percentage of the intracellular protein is secreted.

ii. Cytomegalovirus (CMV) Proteins a. CMV

Human cytomegalovirus (CMV) is a ubiquitous agent in human populations. Infections are generally asymptomatic, but there can be serious medical manifestations of the disease in immunocompromised individuals (transplant recipients and AIDS patients) and in congenitally infected newborns. In immunodeficient patients, primary CMV infection and reactivation of latent virus is associated with serious diseases, including retinitis and pneumonia. CMV infection also predisposes the patient to fungal and bacterial infections. Congenital CMV infection of the fetus occurs in about 1% (36,000) of infants born in the U.S. per year. Of these infants 10–20% will have symptomatic infection at birth or within two years of birth with a mortality rate of 10–15%. Among the survivors, many will have mild to severe neurologic complications including hearing loss, learning disabilities and mental retardation.

CMV has a linear double-stranded genome that is extremely large, with an estimated size of about 240 kbp. Like other herpesviruses, CMV specifies multiple glycoproteins, Stinski, M., J. Virol 19:594–609 (1976); Pereira, L., et al., Infect Immun. 36:933–942 (1982), and these include, but are not limited to, gB and gH. Strains of CMV include AD169 and Towne.

b. CMV gB

The gB gene encodes the p130 CMV protein described by Rasmussen et al., U.S. Pat. No. 5,194,256, and has been identified by nucleotide sequencing, Cranage, M. P. et al., EMBO J. 5:3057–3063 (1986). As described in Spaete, et al., Virology 167:207–405 (1988), sequence analysis of the gB gene reveals that it encodes a protein of about 906–907 amino acids in length, including the signal sequence. This protein is a type I glycoprotein with an N-terminal hydrophobic signal sequence (comprising amino acids $Met_{-24}$ to $Ser_{-1}$), an extracellular domain (comprising amino acids $Ser_1$ to $Asp_{690}$), a second hydrophobic, transmembrane domain (residues $Leu_{691}$ to $Tyr_{748}$), and a C-terminal cytoplasmic domain (residues $Thr_{749}$ to $Val_{884}$). The extracellular domain contains 19 potential N-linked glycosylation sites. The transmembrane region is likely to span the membrane three times as has been proposed for the HSV gB protein analog.

The mature CMV gB protein contains 12 cysteine and 19 proline residues in the extracellular domain, and the location of 10 of these cysteines and 7 of these prolines is conserved for at least six herpesvirus gB protein analogs.

Pulse chase studies of CMV infected cells revealed that mature gB is proteolytically processed from a 130–160 kD protein, designated gp130, to a two-chain, disulfide-linked molecule containing gp55, representing the carboxyl terminal region of the larger precursor molecule, and a 93-kD chain representing the amino terminal region. The cleavage results from a trypsin-like proteolysis between $Arg_{436}$ and $Ser_{437}$. This proteolysis occurs when gB is expressed alone in CHO cells as a truncated molecule, where the carboxyl terminal region, including the transmembrane domain of gB, is removed and the cleavage site is intact, and thus must be due to host cell proteases. For examples of truncated gB proteins, as well as proteins with modified endoproteolytic cleavage site such that cleavage of the gB protein is effectively inhibited, see PCT Publ. No. WO 89/07143, published Aug. 10, 1994, owned by the present assignee.

c. CMV gBdTM

Figure 10:
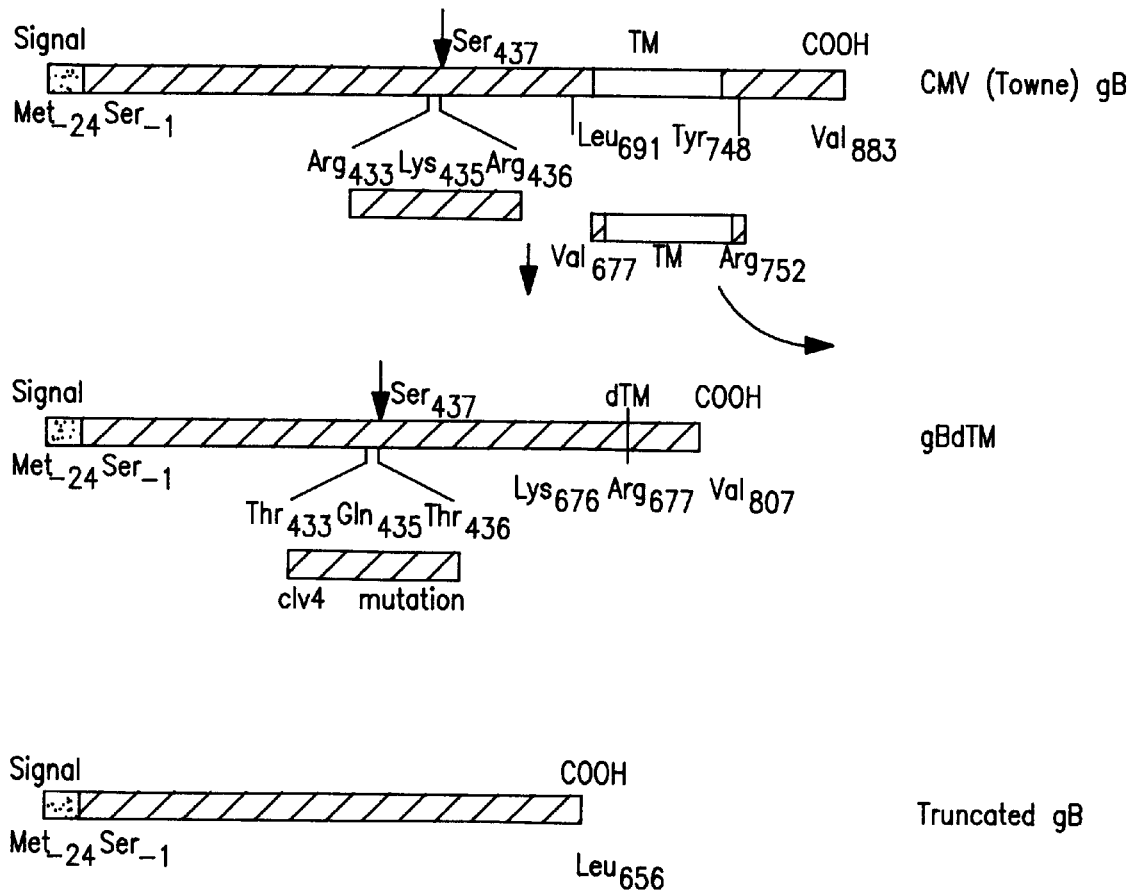
FIG. 10 is a comparison of full-length CMV gB protein and truncated gB protein with the present invention, gBdTM.
Figure 11:
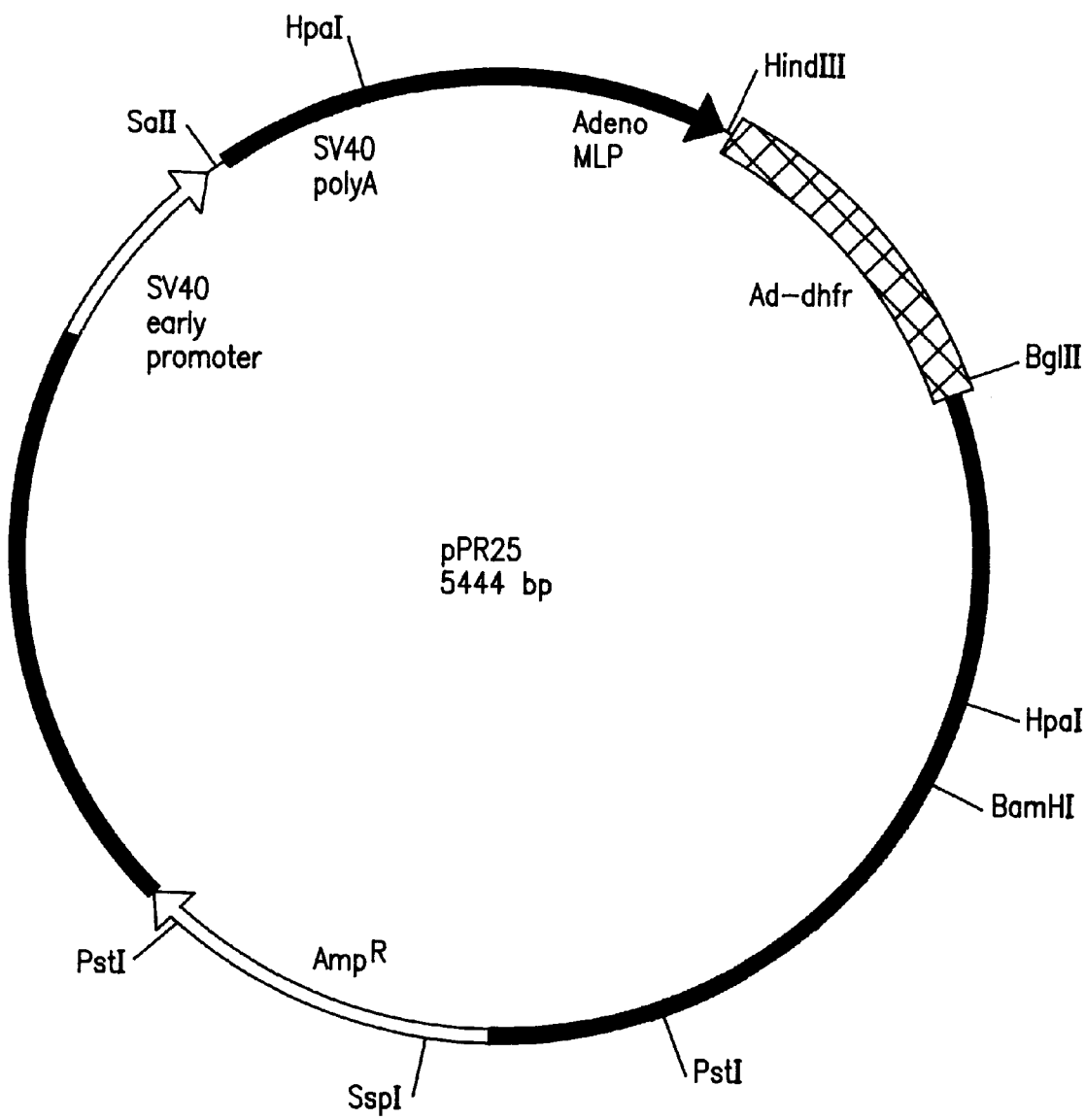
FIG. 11 is the expression vector pPR25.
Figure 12:
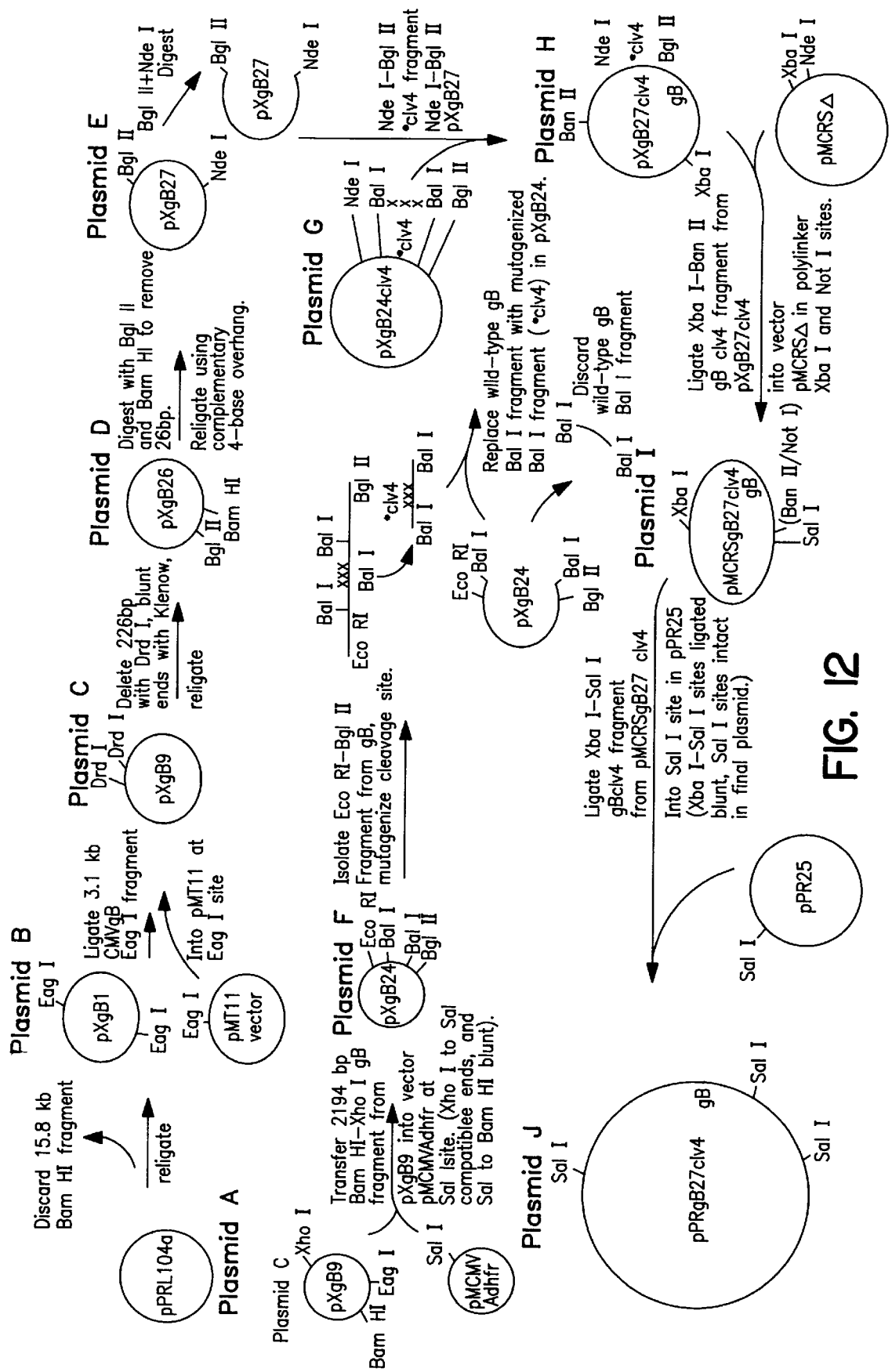
FIG. 12 is the construction of CMV plasmid pPRgB27clv4.

The present invention is exemplified by CMV gB modification introduced by the deletion of the transmembrane region such that the resulting protein derivative was efficiently secreted into the medium rather than being retained on the cell surface. To remove the normal proteolytic processing site, three site-specific point mutations were made in the gB gene, resulting in three specific amino acid changes as follows: $Arg_{433}$ to $Thr_{433}$, $Lys_{435}$ to $Gln_{435}$, and $Arg_{436}$ to $Thr_{436}$. To remove the transmembrane region, nucleotides encoding amino acids $Val_{677}$ through $Arg_{752}$ were deleted, resulting in a gB derivative protein where the extracellular domain was directly fused to the cytoplasmic domain. The gB derivative gene was placed under the control of the SV40 early promoter in the mammalian cell expression plasmid pPR25 to yield the final expression plasmid pPRgB27clv4. This vector also contains the dihydrofolate reductase cDNA which introduces a marker gene suitable for plasmid selection and amplification. A schematic representation of the gB derivative protein ("gBdTM") compared to the full-length gB protein and truncated gB protein is shown in FIG. 10. The plasmid map of the expression vector, pPR25 is shown in FIG. 11. The cloning of the gB derivative gene and the derivation of the final expression plasmid pPRgB27clv4 are described in detail below. FIG. 12 outlines this entire process.

d. Construction of plasmid pPRgB27clv4

Figure 13:
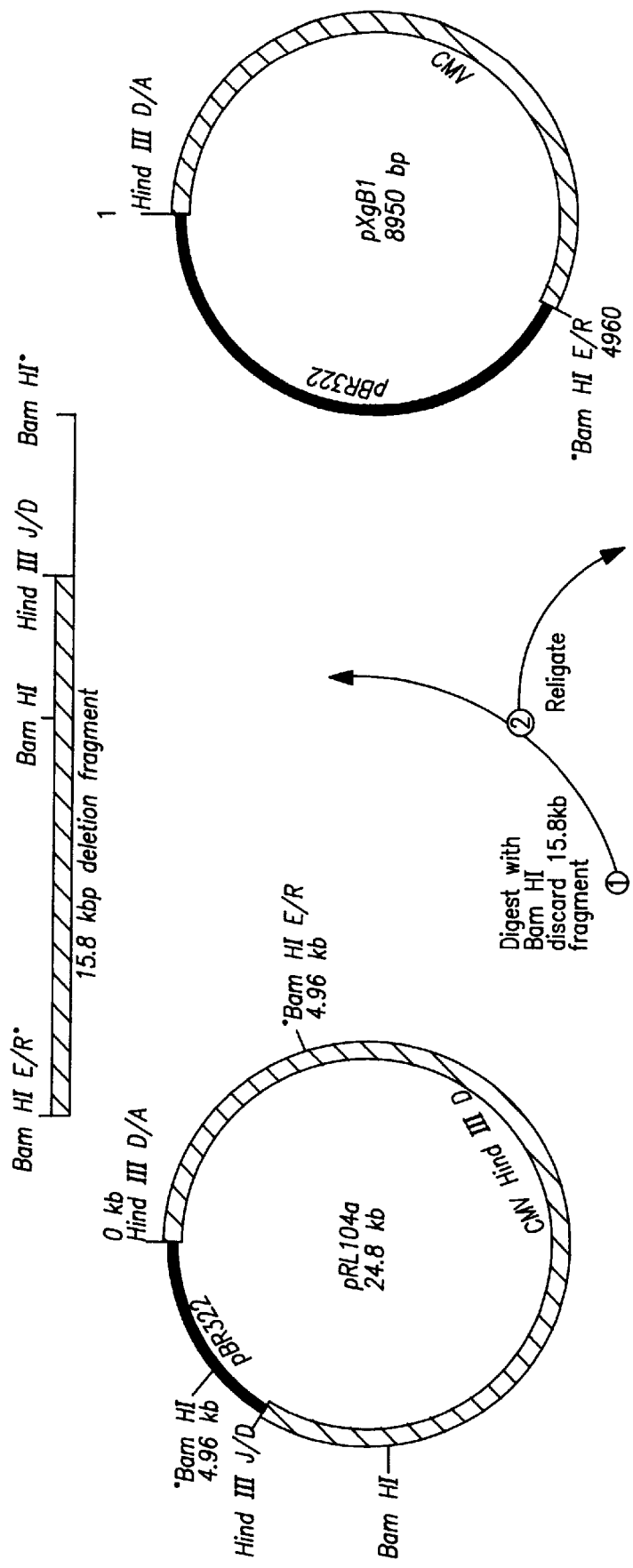

Plasinid pRL104a (FIG. 13) was digested with restriction enzyme Bam HI and religated to generate pXgB1 that retains the complete CMV gB coding gene on a 4.96-kbp Hind III D/A to Bam HI E/R CMV fragment. Plasmid pXgB1 lacks a 15.8-kbp Bam HI fragment from pRL104a.

Figure 14:
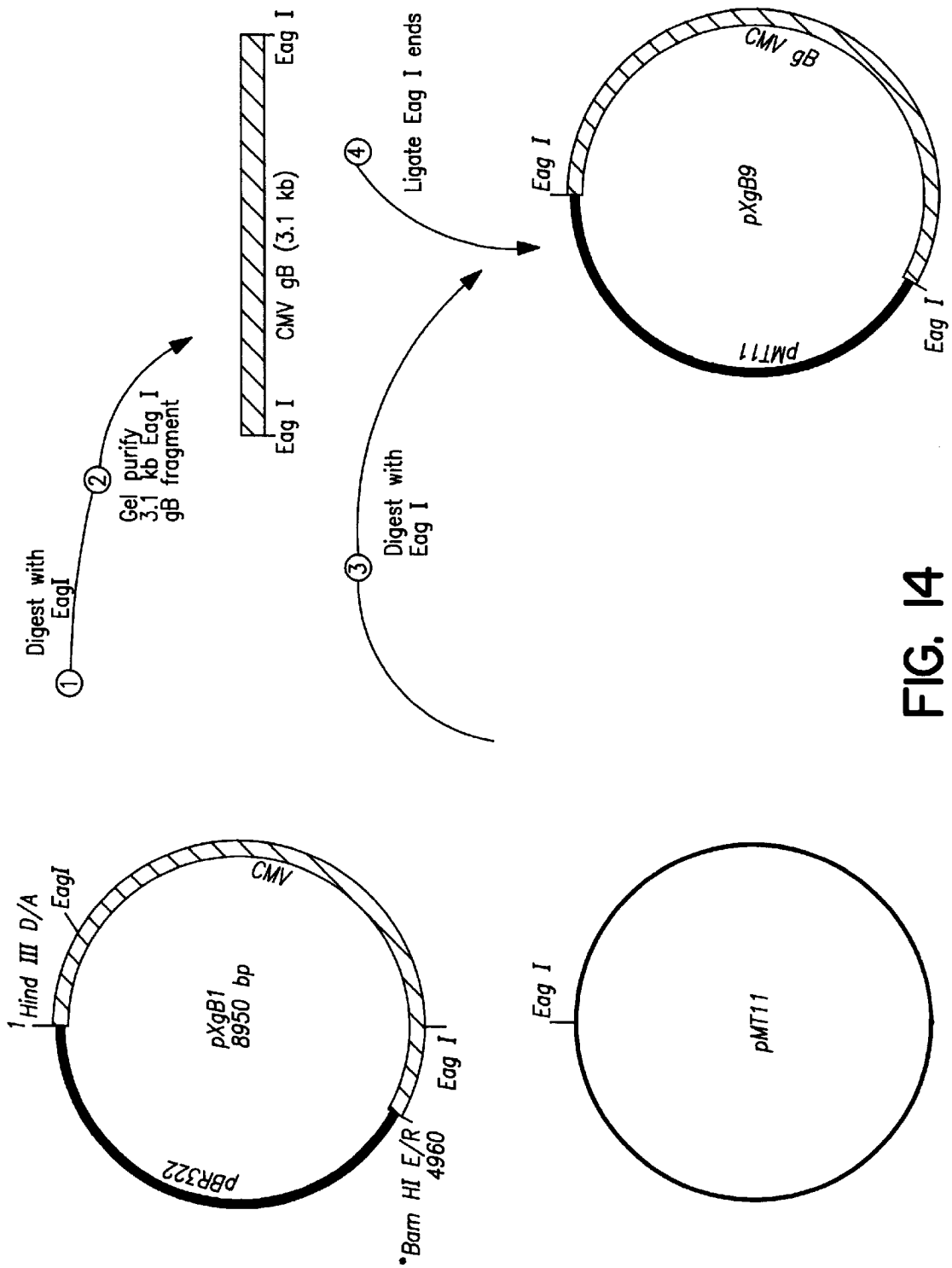
FIG. 14 is the construction of plasmid pXgB9.

Plasmid pXgB9 (FIG. 14) contains a 3.1-kbp Eag I fragment of CMV inserted into a plasmid staging vector, pMT11. This construct was cloned by digestion of plasmid pXgB1 with Eag I, isolation of a 3.1-kbp CMV gB fragment, digestion of the vector pMT11 with Eag I, and cloning of the 3.1-kbp fragment into the Eag I site in pMT11.

Figure 15:
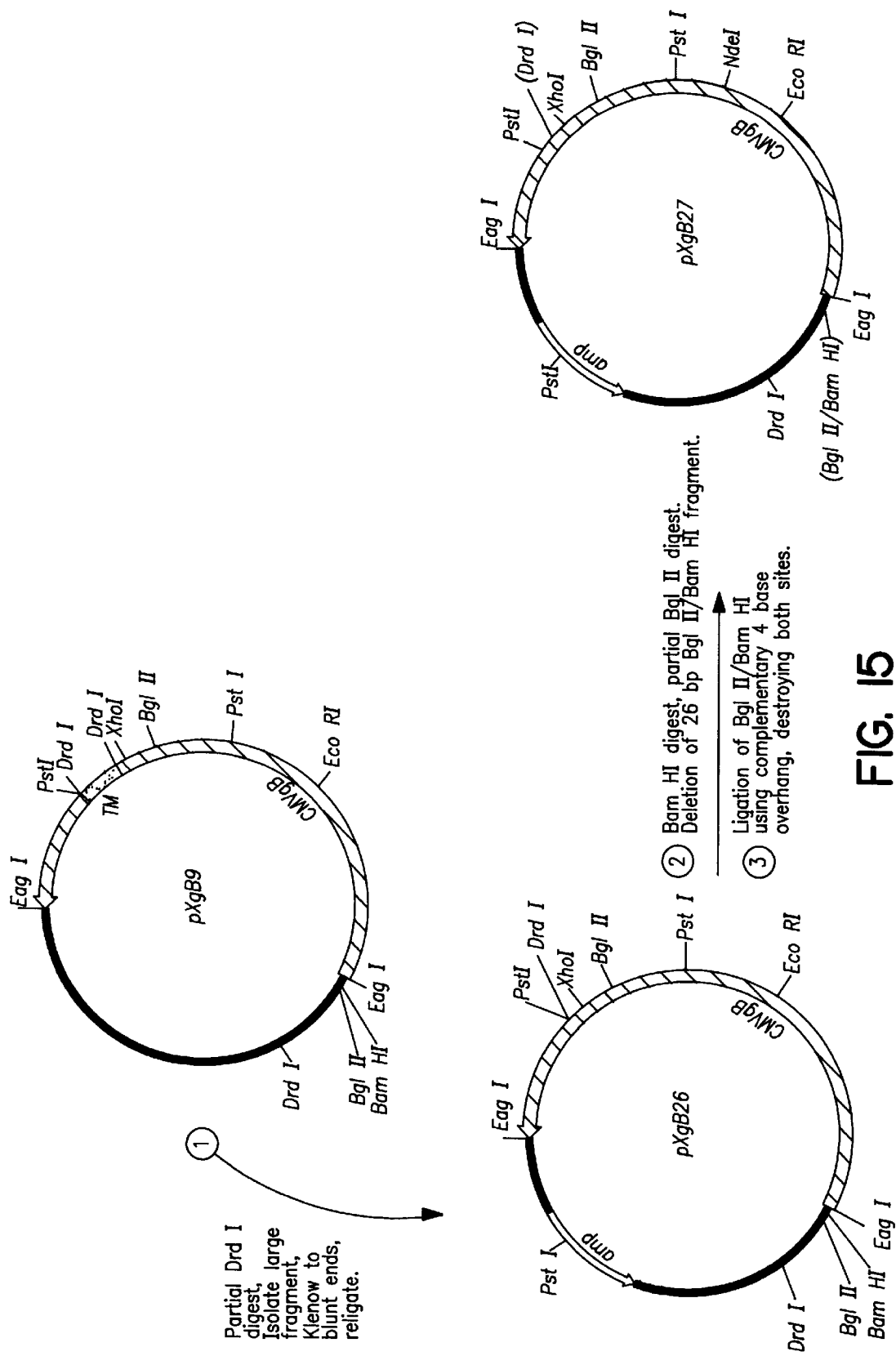
FIG. 15 is the construction of plasmid pXgB26.

Plasmid pXgB26 (FIG. 15) was constructed by partial digestion of pXgB9 with Drd I, resulting in the deletion of a 226 bp fragment. The large (5.1-kbp) plasmid fragment was isolated, the ends were digested with Klenow and the plasmid was religated. The resulting deletion removes those DNA sequences encoding the transmembrane region of CMV (Towne) gB. Plasmid pXgB27 was constructed as a staging plasmid for subcloning CMV gB. This plasmid was constructed from plasmid pXgB26 by deletion of a 39-bp Bam HI-Bgl II fragment in the polylinker, followed by religation. Plasmid pXgB26 was completely digested with Bam HI, then partially digested with Bgl II, the large plasmid fragment was gel purified, and the complementary 4-base overhanging ends were ligated together, destroying both restriction sites. The resultant plasmid has a unique Bgl II site contained within the gB gene.

Figure 16:
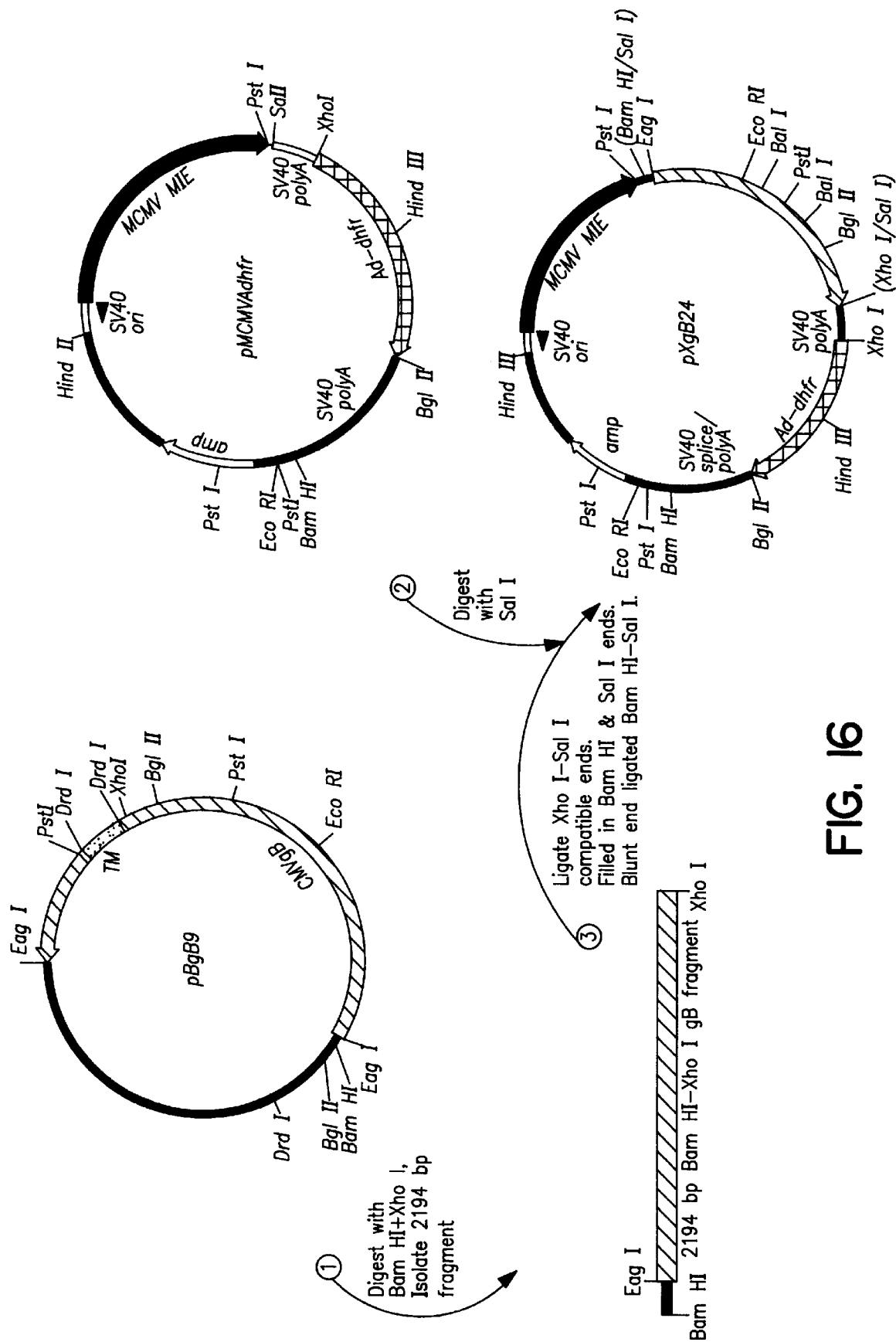
FIG. 16 is the construction of plasmid pXgB24.

Plasmid pXgB24 (FIG. 16) was constructed from pXgB9 and vector plasmid pMCMVAdhfr. Plasmid pXgB9 was digested with Bam HI and Xho I, and the 2194-bp CMV gB fragment was isolated by gel purification. The vector plasmid pMCMVAdhfr was digested with Sal I, and ligated to the 2194-bp Xho I to Sal I gB fragment. The free Bam HI and Sal I ends were then filled with Klenow and ligated together resulting in plasmid pXgB24.

Figure 17:
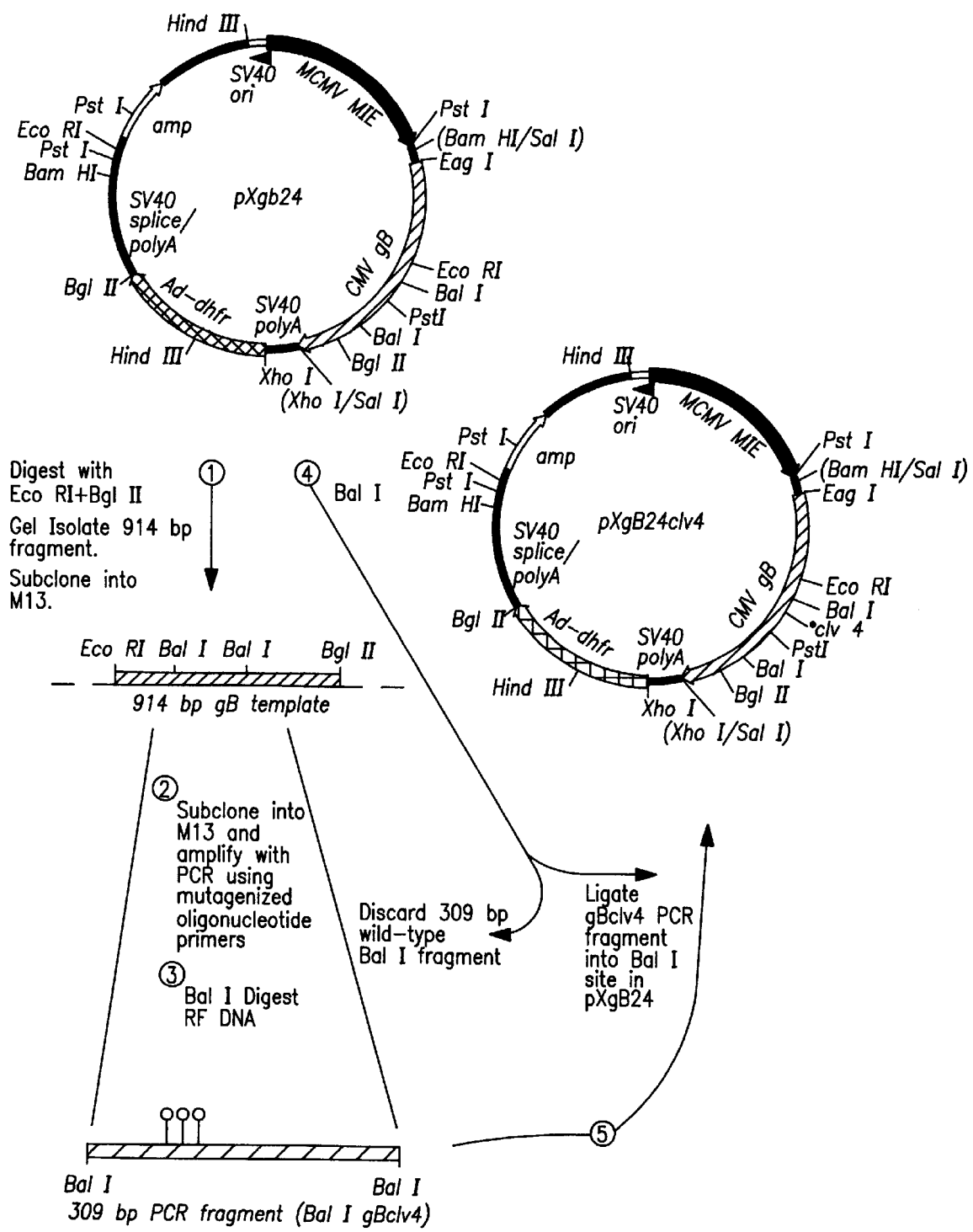
FIG. 17 is the construction of plasmid pXgB24clv4.

Plasmid pXgB24clv4 (FIG. 17) contains the CMV gB gene, truncated at the carboxyl terminus, with three site-specific point mutations engineered to modify the proteolytic cleavage site in the expressed gB protein. It contains nucleic acids encoding a 680 amino acid gB protein and four additional amino acids, Asp-Leu-Asp-Lys at the carboxyl terminal end, derived from the polylinker in the vector. The plasmid contains the murine cytomegalovirus major immediate early (MCMV MIE) promoter system driving the gB gene, and the adenovirus dihydrofolate reductase (Ad-dhfr) gene for use as a selectable marker for amplification of the gB gene in dhfr CHO cells. It also contains the SV40 polyadenylation (SV40 polyA) and origin of replication (ori) genes, and an ampicillin resistance gene.

Plasmid pXgB24 was digested with Eco RI and Bgl II, and a 914-bp gB fragment was gel purified, subcloned into M13 and used as a template for PCR. Double stranded M13mpl8 containing the CMV gB template was combined with synthetic oligonucleotide primers containing the mutagenized cleavage sequence and amplified by PCR. The resultant DNA fragment was then digested with Bal I, the 309-bp mutagenized fragment was isolated, and exchanged with the analogous wild type 309-bp Bal I fragment in pXgB24, resulting in plasmid pXgB24clv4. The cleavage mutation was confirmed by sequencing.

Figure 18:
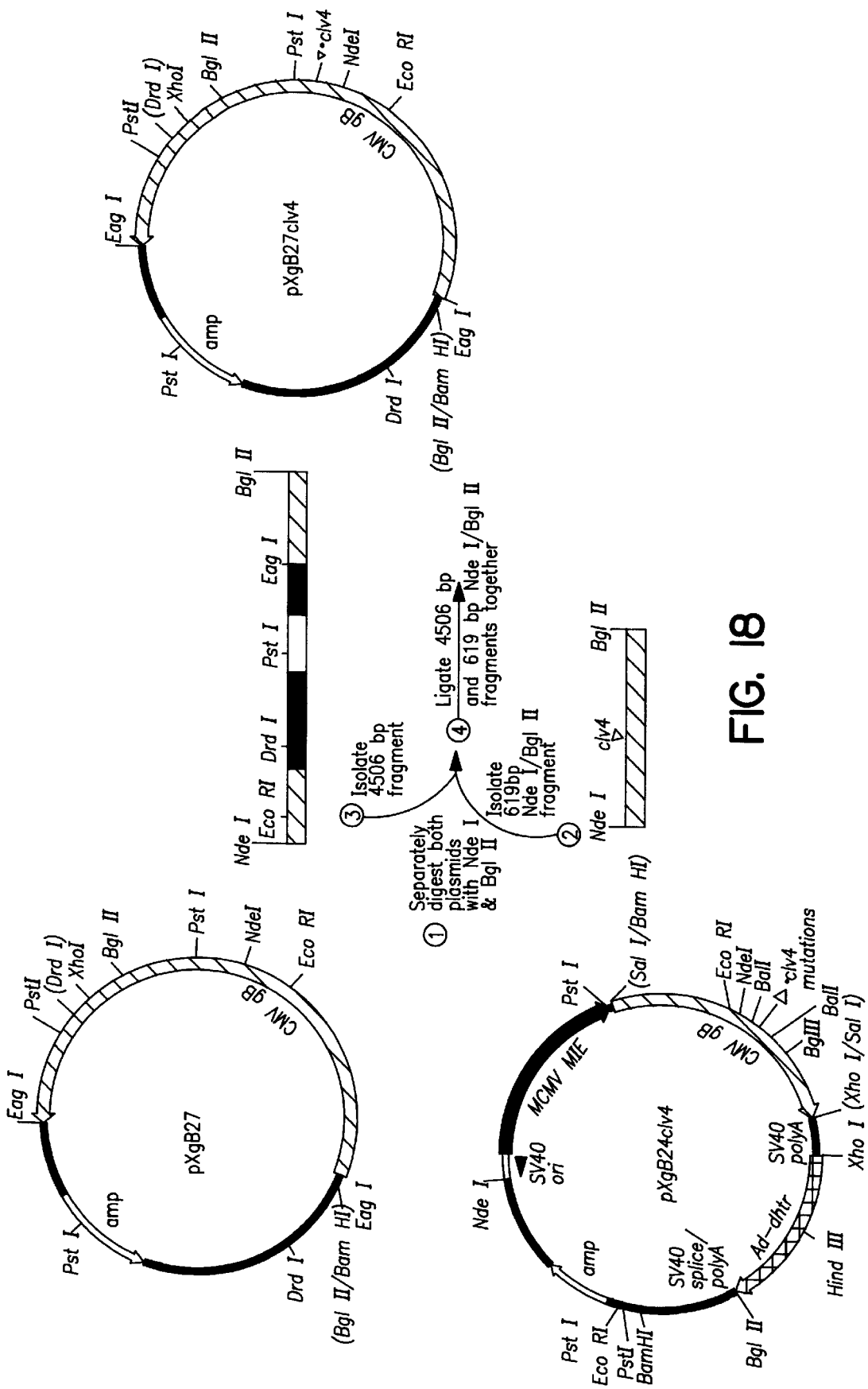
FIG. 18 is the construction of plasmid pXgb27clv4.

Plasmid pXgB27clv4 (FIG. 18) was constructed from pXgB27 and pXgB24clv4 as follows. Plasmid pXgB27 was digested with Nde I and Bgl II and a 4506-bp gB fragment was gel isolated. Meanwhile, pXgB24clv4 was also digested with Nde I and Bgl II and a 619-bp fragment was gel isolated. These two Nde I-Bgl II fragments were then ligated together to generate pXgB27clv4. This plasmid contains the modified full-length gB with the three site-specific point mutations and the transmembrane deletion described above.

Figure 19:
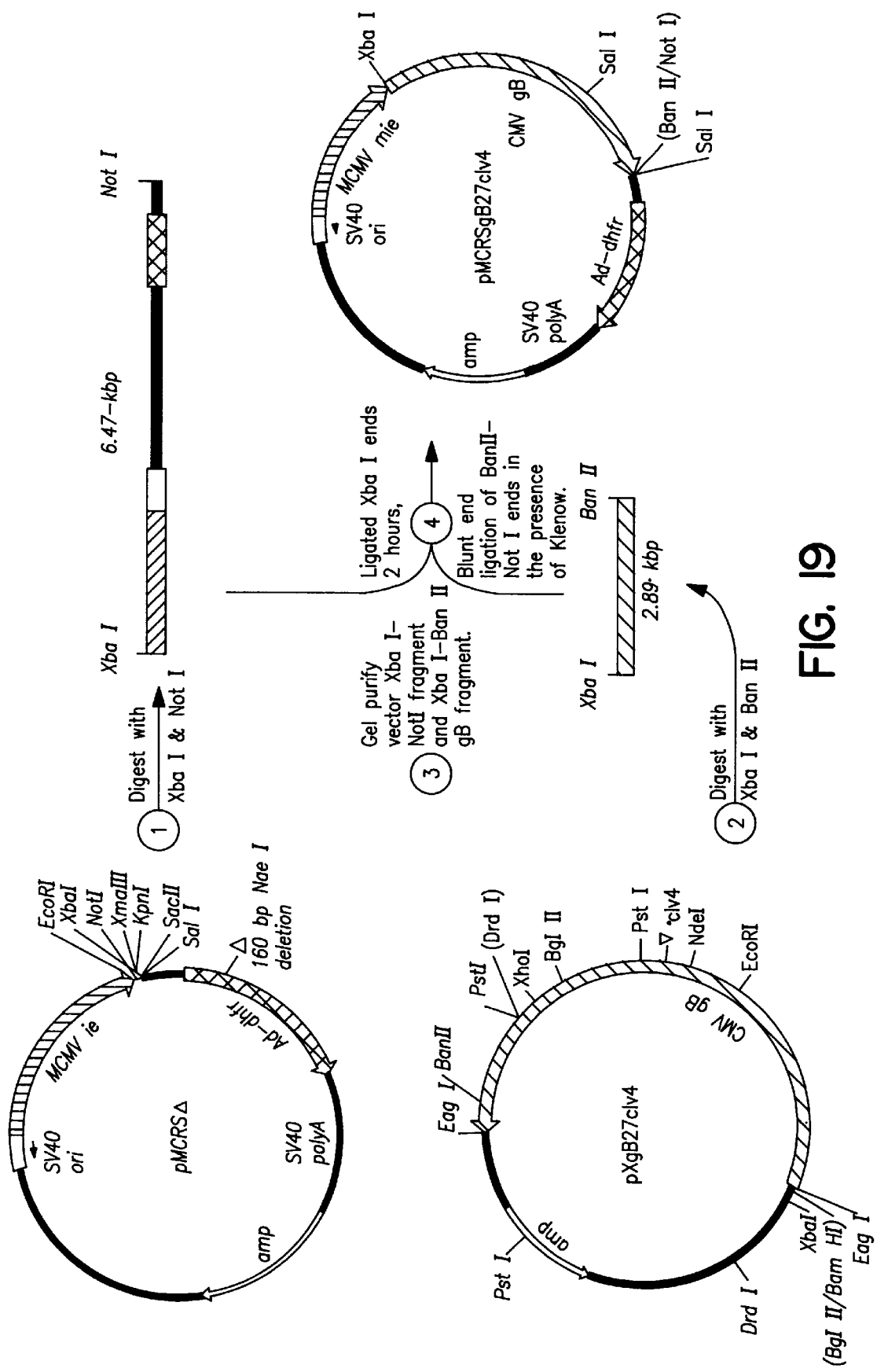
FIG. 19 is the construction of plasmid pMCRSgB27clv4.

The scheme used to construct pMCRSgB27clv4 is outlined in FIG. 19. The full-length, cleavage mutant derivative of the gB gene was obtained as a 2.89-kbp Xba I-Ban II fragment from plasmid pXgB27clv4. Mammalian expression vector plasmid pMCRSΔ was digested with Xba I and Not I, and a 6.47-kbp vector fragment was gel purified. The 2.89-kbp Xba I-Ban II fragment was ligated into the 6.47-kbp vector in two steps. First, the Xba I ends were allowed to ligate for two hours. Then ligation was continued overnight in the presence of Klenow to blunt the Ban II and Not I termini and join them, destroying both sites, and resulting in pMCRSgB27clv4. This plasmid is 9.36 kbp and contains the murine CMV major immediate early promoter (MCMV MIE), the SV40 origin of replication and polyadenylation sequences, and the dihydrofolate reductase (DHFR) cDNA under the control of the adenovirus-2 major late promoter derived from pPR25. Plasmid pPR25 is a mammalian cell expression vector containing the dihydrofolate reductase (DHFR) cDNA under the control of the adenovirus-2 major late promoter (Ad-2 MLP), SV40 DNA encoding the small T antigen intron and polyadenylation sequences. The construction of pPR25, discussed above, required the digestion of plasmid pPR21 with Stu I and the insertion of a 3388 bp Nru I-Eco RI fragment from pAd-dhfr. Plasmid pPR21 was derived from pSV7d by inserting a synthetic 85-mer, containing the bla promoter and the restriction sites for Stu I and Xho I, into the Ssp I site in the polylinker. Plasmid pSV7d is a mammalian cell expression vector which contains the SV40 origin of replication and early promoter (315 bp, Pvu II pos. 272- Stu I 5193, with an 8 bp deletion between nucleotides 173 and 182), a polylinker, and the early region SV40 poly A addition site (217 bp, Bcl I pos. 2775–pos. 2558) cloned into the pBR322 derivative pML between nucleotide 4210 and Nru I pos. 973. The SV40 sequences are positioned such that the direction of transcription from the early promoter is in the same direction as the ampicillin gene of the vector.

Figure 20:
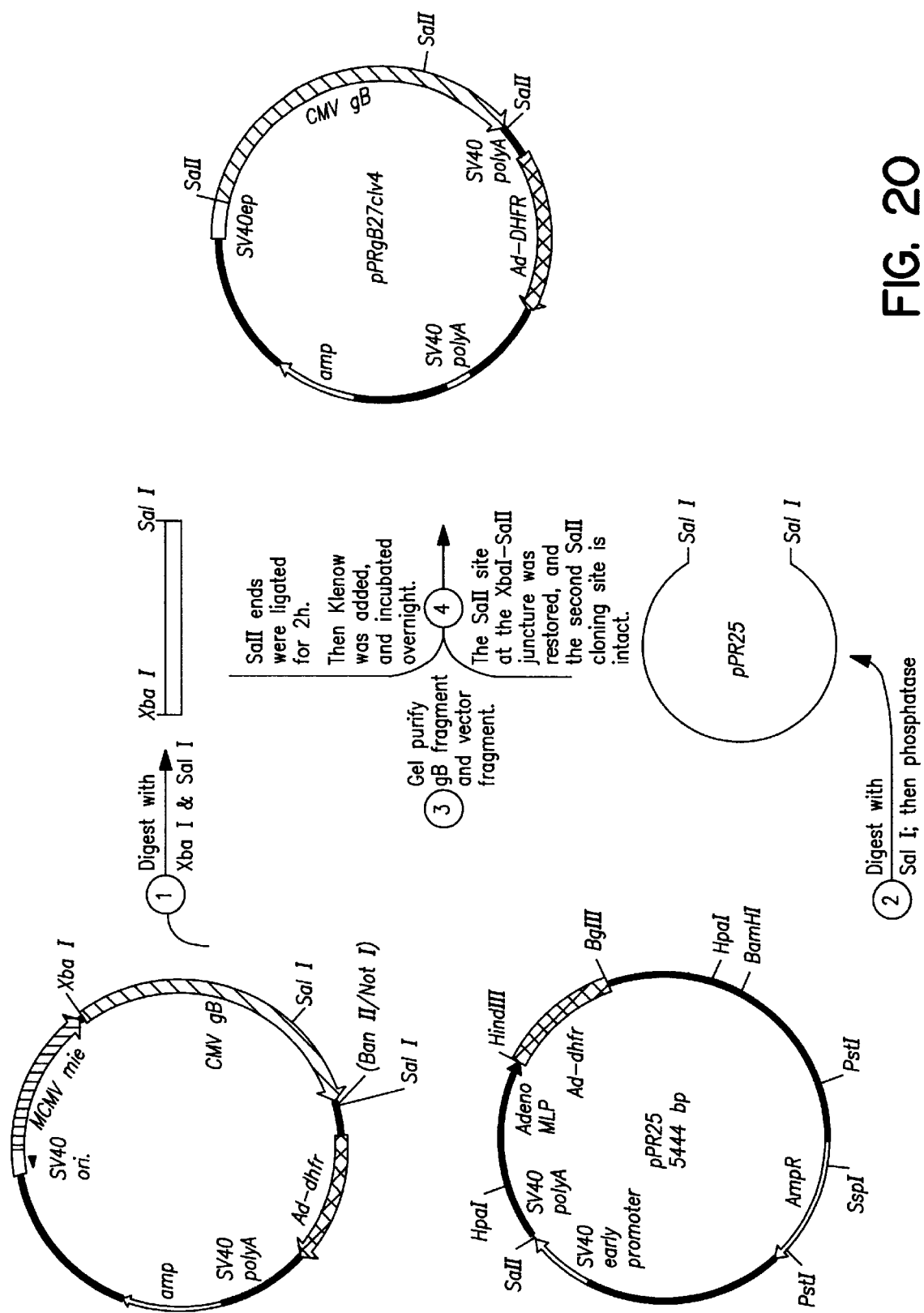
FIG. 20 is the construction of plasmid pPRgB27clv4.
Figure 21:
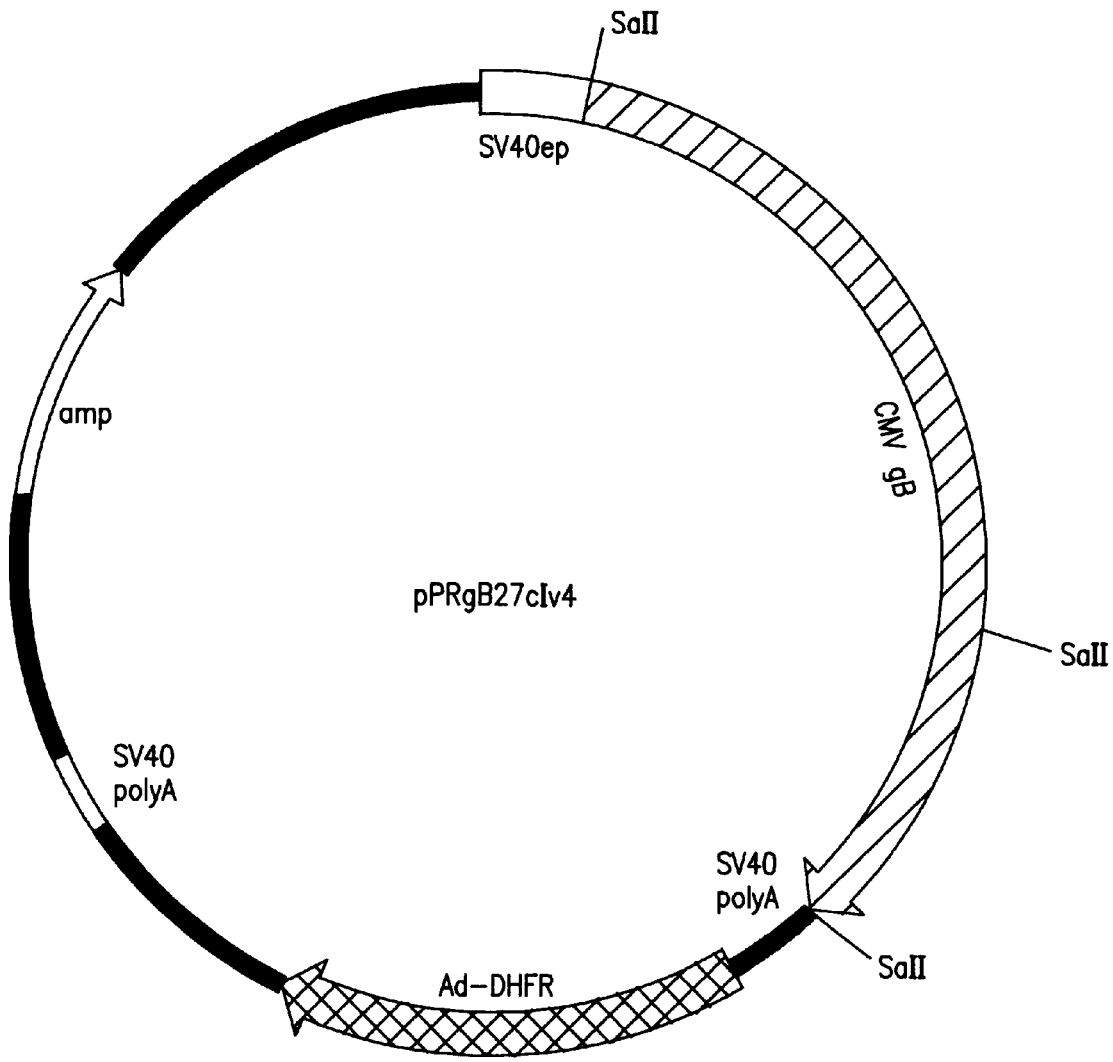
FIG. 21 is the expression vector pPRgB27clv4.

Plasmid pPRgB27clv4, the mammalian expression plasmid for the CMV gB antigen, contains the modified full-length derivative of the gB gene with the cleavage mutation and the transmembrane deletion (gBdTM), as described above, under the control of the SV40 early promoter. This plasmid was derived from pPR25, a mammalian cell expression vector. Plasmid pMCRSgB27clv4 (FIG. 20) was digested with Xba I and Sal I, and a 2.90-kbp CMV gB fragment was gel purified. Expression vector pPR25 was digested with Sal I, phosphatased and ligated with the 2.90-kbp CMV gB fragment resulting in plasmid pPRgB27clv4. This final expression plasmid, pPRgB27clv4 is 8.35-kbp and contains the Ad-dhfr gene for selection and amplification purposes as described above. The plasinid map of pPRgB27clv4 is shown in FIG. 21.

e. Expression of pPRgB27clv4 in mammalian cells

A CHO cell line expressing a secreted derivative of CMV glycoprotein gB was selected for large scale commercial production. For this purpose, CHO cells lacking an endogenous dihydrofolate reductase (dhfr enzyme) were transfected with a DNA plasmid vector containing genes for both dhfr as well as a CMV gB derivative termed gBdTM. The transfected cells were grown in selective culture medium such that only cells that expressed dhfr could grow. The level of gB production by these cells was increased by a stepwise process of culture in selective medium containing increasing concentrations of the drug methotrexate (MTX), a noncompetitive inhibitor of dhfr. Cells acquired the ability to grow in the presence of MTX by amplifying the number of copies of the dhfr gene, Alt, F. W., et al., J. Biol. Chem. 235:1357–1370 (1978); Kaufman, R. J., et al., Mol. Cellular Biol. 1:1069–1076 (1981). A second gene, gB, that was directly linked to the dhfr DNA was also co-amplified, Kaufman, R. J., et al., J. Mol. Biol. 159:601–621 (1982). This process entailed exposure of cells in a bulk population to selective medium with MTX, selection of 50–400 discrete single colony clones, expansion of the colony cell number by serial passage in 96-well plates, then 24-well and 6-well plates with concurrent evaluation of gB productivity using an ELISA assay to measure the amount of gB secreted into the culture medium. This process was stopped when no further gains in productivity were observed.

f. Radioimmunoprecipitation of cell lines expressing truncated gB and gBdTM expressing CMV To analyze the expression and secretion efficiency of the CHO cell lines expressing CMV gB, cell lines transfected with control plasmid pPR25; transinembrane-deleted CMV gB (gBdTM) plasmid pPRgB27clv4 encoding a gB molecule lacking amino acids $Val_{677}$ through $Arg_{752}$; and truncated CMV gB plasmid pXgB24clv4 encoding a gB molecule lacking amino acids $Leu_{657}$ through $Val_{883}$ were radioimmunoprecipitated as follows.

For radiolabeling with [$^{35}$S]-methionine, cells were grown to 65% confluence in 6 cm dishes, washed once with 2 mL medium (Delbucco's Modified Eagle medium (DME) lacking methionine, containing 10% dialyzed fetal bovine serum (FBS) supplemented with 200 μg/mL of L-proline, 2 mM L-glutamine, 100 U/mL penicillin, and 100 μg/mL streptomycin), then 1 mL of labeling medium (DME supplemented as above, containing 250 μCi/mL [$^{35}$S]-methionine, (>1000 Ci/mmol) from Amersham # SJ.1515) was applied to cell monolayers and incubated at 37° C. for 4 hours. Cell media were collected, placed on ice and centrifuged for five minutes at 4° C., and supernatants were transferred to fresh tubes, treated with protease inhibitors (Boehringer Mannheim) to a final concentration of 17 μg/mL aprotinin, 1 μg/mL pepstatin, and I mM PMSF, and stored at −80° C. Cell lysates were prepared by addition of 200 μL chilled (4° C.) lysis buffer (100 mM NaCl, 20 mM Tris, pH 7.5, 1 mM EDTA, 0.5% NP40, 0.5% sodium deoxycholate (DOC), 17 μg/mL aprotinin, 1 μg/mL pepstatin, 1 mM PMSF), to each dish and scraping the cells off of the dish with a disposable cell scraper. The cells were transferred to eppendorf tubes on ice, the dishes were washed with another 200 μL of lysis buffer, and the contents were transferred into the appropriate tubes and kept on ice for 10 minutes with occasional vortexing. The lysates were clarified by centrifugation for 10 minutes at 4° C. in an Eppendorf centrifuge to remove insoluble debris. The supernatants (lysates) were transferred to fresh tubes and quick frozen at −80° C. The serum was obtained from HyClone Laboratories, Inc. Logan, Utah. All other ingredients were supplied by Sigma Chemical Co., St. Louis, Mo., unless otherwise noted.

For immunoprecipitation, cell lysates (200 µL) and media (500 µL) were mixed together with 100 µL and 250 µL respectively, of a 20% solution of protein A sepharose (PAS) in lysis buffer, and rocked gently at 4° C. for 1 hour. The PAS was removed by centrifugation for 1 min. at 14,000×g and the supernatants were transferred to fresh tubes and mixed together with 2 µL and 4 µL respectively, of CMV gB specific monoclonal antibody 15D8 ascites, Rassmussen, L. Virol. 55, 274–280, (1985), and rocked overnight at 4° C. PAS was added to each tube, 140 µL and 350 µL respectively, and rocked 1 hour as above. PAS-immune complexes were collected by centrifugation, washed 3× in lysis buffer lacking BSA and protease inhibitors, and once in 120 mM Tris HCI, pH 8. Immunoprecipitated proteins were released from protein A Sepharose by boiling in SDS sample buffer, followed by polyacrylamide gel electrophoresis (SDS-PAGE) analysis on a 10% polyacrylamide gel.

The results showed that the majority of the CMV gB (about 110 kD) from the cell line expressing truncated gB was retained inside the cells whereas only a fraction was secreted into the medium. Comparitively, the cell line expressing CMV gBdTM showed at least a 5 to 10-fold increase in secreted gB as well as a large increase in overall expression.

What is claimed is:

1. A method of increasing the secretion of a viral protein comprising:

(a) providing a population of host cells transformed with a recombinant vector, wherein said vector comprises a polynucleotide linked in proper reading frame to control sequences whereby the polynucleotide can be transcribed and translated in the host cell, wherein the polynucleotide encodes a viral protein selected from the group consisting of a cytomegalovirus (CMV) gB, and a CMV gB with a modified endoproteolytic cleavage site such that cleavage of the gB protein is inhibited, wherein the viral protein lacks a transmembrane-encoding domain but comprises a sequence encoding substantially all of an homologous C-terminal cytoplasmic domain; and (b) culturing the population of cells under conditions whereby the protein encoded by the polynucleotide is expressed and secreted, wherein the protein is secreted at a higher level than the corresponding protein which comprises truncation of both the transmembrane domain and the C-terminal cytoplasmic domain.

2. The method of claim 1, wherein a sequence encoding a native N-terminal signal domain of the viral protein is replaced with a heterologous signal domain.

3. The method of claim 1, wherein a sequence encoding an N-terminal signal domain is from that of a viral protein other than the protein encoded by the remaining sequence.

4. The method of claim 3, wherein the polynucleotide encodes a CMV gB.

5. The method of claim 1, wherein the polynucleotide encodes a CMV gB with a modified endoproteolytic cleavage site such that cleavage of the gB protein is inhibited.

* * * * *